(12) United States Patent
Eicher et al.

(10) Patent No.: US 12,030,679 B2
(45) Date of Patent: Jul. 9, 2024

(54) METHOD FOR PRODUCING A CARTRIDGE

(71) Applicant: Boehringer Ingelheim International GmbH, Ingelheim am Rhein (DE)

(72) Inventors: Joachim Eicher, Ingelheim am Rhein (DE); Gilbert Wuttke, Ingelheim am Rhein (DE); Herbert Graessl, Murrhardt (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 434 days.

(21) Appl. No.: 17/413,224

(22) PCT Filed: Dec. 13, 2019

(86) PCT No.: PCT/EP2019/085001
§ 371 (c)(1),
(2) Date: Jun. 11, 2021

(87) PCT Pub. No.: WO2020/126864
PCT Pub. Date: Jun. 25, 2020

(65) Prior Publication Data
US 2022/0135261 A1  May 5, 2022

(30) Foreign Application Priority Data
Dec. 18, 2018 (EP) ..................................... 18213552

(51) Int. Cl.
*B65B 3/00* (2006.01)
*A61M 11/00* (2006.01)
(Continued)

(52) U.S. Cl.
CPC .......... *B65B 3/003* (2013.01); *A61M 11/007* (2014.02); *B05B 11/0054* (2013.01);
(Continued)

(58) Field of Classification Search
CPC .. B65B 3/003; B65B 3/30; B65B 7/28; B65B 7/2821; B05B 11/0054; B05B 11/028; A61M 11/007; A61M 2207/00
(Continued)

(56) References Cited

U.S. PATENT DOCUMENTS 3,731,453 A * 5/1973 Porteous ................. A61M 5/00
53/471
5,548,943 A * 8/1996 Behar et al. .......... B05B 11/028
53/473
(Continued)

FOREIGN PATENT DOCUMENTS

EP    1091809 B1 * 9/2003 ......... B05B 11/0064
EP    2614848 A1    7/2013
(Continued)

OTHER PUBLICATIONS

International Search report and Written Opinion for corresponding PCT Application No. PCT/EP2019/085001, 12 pages dated May 4, 2020.

*Primary Examiner* — Stephen F. Gerrity
(74) *Attorney, Agent, or Firm* — Matthew B. Dernier, Esq.

(57) ABSTRACT

A method for producing a cartridge is proposed, where a fluid is filled into an opening of a container and a closure part is inserted into the container, thereby moving a movable piston arranged within the container.

29 Claims, 10 Drawing Sheets

(51) Int. Cl.
*B05B 11/00* (2023.01)
*B05B 11/02* (2023.01)
*B65B 3/30* (2006.01)
*B65B 7/28* (2006.01)
*B05B 11/10* (2023.01)
*B05B 15/40* (2018.01)

(52) U.S. Cl.
CPC .............. *B05B 11/028* (2023.01); *B65B 3/30* (2013.01); *B65B 7/28* (2013.01); *A61M 2207/00* (2013.01); *A61M 2209/045* (2013.01); *B05B 11/1091* (2023.01); *B05B 15/40* (2018.02)

(58) Field of Classification Search
USPC .................... 53/471, 489, 319, 320, 284
See application file for complete search history.

(56) References Cited

U.S. PATENT DOCUMENTS

| | | | | |
|---|---|---|---|---|
| 10,092,921 | B2* | 10/2018 | Muller | A45D 34/00 |
| 11,207,474 | B2 | 12/2021 | Dunne | |
| 2002/0128595 | A1* | 9/2002 | Weston et al. | B65B 3/003 604/72 |
| 2008/0035233 | A1* | 2/2008 | Luthi et al. | B65B 3/003 141/286 |
| 2011/0247722 | A1* | 10/2011 | Stepovich et al. | A61M 5/1782 141/2 |
| 2013/0008924 | A1* | 1/2013 | Lafosse | B65D 83/0033 222/386 |
| 2013/0218066 | A1* | 8/2013 | Duquet et al. | A45D 34/04 604/20 |
| 2015/0122847 | A1* | 5/2015 | Pritchett et al. | B05B 11/028 222/383.1 |
| 2017/0203056 | A1 | 7/2017 | Dunne | |
| 2017/0209892 | A1 | 7/2017 | Kladders | |

FOREIGN PATENT DOCUMENTS

| | | |
|---|---|---|
| GB | 2503028 A | 12/2013 |
| JP | 0775672 A | 3/1995 |
| JP | H0775672 A * | 3/1995 |
| JP | 2017521195 A | 8/2017 |
| WO | 8402079 A1 | 6/1984 |
| WO | 2009115200 A1 | 9/2009 |
| WO | 2010022870 A1 | 3/2010 |
| WO | 2011069635 A2 | 6/2011 |
| WO | 2012162305 A1 | 11/2012 |

* cited by examiner

METHOD FOR PRODUCING A CARTRIDGE

BACKGROUND

The present invention relates to a method for producing, in particular filling, a cartridge.

In particular, the present invention relates to the filling of a cartridge with a fluid, preferably a liquid, in particular a liquid pharmaceutical composition/formulation and/or a liquid medicament, preferably wherein the cartridge is to be used together with a nebulizer/dispensing device for nebulizing/dispensing of the fluid.

WO 2009/115200 A1 discloses a method of filling a reservoir with a fluid, wherein a fluid chamber in form of a collapsible bag is pre-collapsed and filled with an initial amount of the fluid which is less than the maximum volume of the fluid chamber in order to avoid an undesirable rise in pressure.

WO 2011/069635 A2 discloses a method for filling a container with a liquid drug from a drug reservoir, wherein the volume of the container is repeatedly reduced and increased in order to displace the liquid drug from the drug reservoir into the container. In this way, the risk of a formation of foam and air bubbles within the liquid drug is reduced.

WO 84/02079 A1 discloses a method for assembling a syringe cartridge. A lower open end of the cartridge is closed by a plunger piston. The cartridge is filled via an upper open end until a fill level is reached. Then, a syringe cartridge closure is provided to close the upper open end. The syringe cartridge closure comprises a displacement dome and a contents displacement trap. Upon closure of the cartridge by means of the syringe cartridge closure, the displacement dome displaces a minor amount of fluid into the contents displacement trap. This seals the cartridge and insures zero head space.

WO 2010/022870 A1 discloses a method for closing an injection cartridge. A proximal open end of the cartridge is closed by a piston comprising a syringe plunger. The distal open end is closed by inserting a rubber stopper, thereby sealing the cartridge, and a housing insert is placed into a void space of the rubber stopper. Then, an aluminium cap having an inserted rubber sealing disc and a central opening which is covered by an attached film seal is placed over the top of the cartridge assembly and subsequently crimped to fix the closure system to the cartridge. The cartridge comprises a further piston arranged between the rubber stopper and the piston having the syringe plunger, which divides the inside of the cartridge into two fluid chambers.

Object of the present invention is to provide an improved method for producing/filling a cartridge, preferably wherein a fast, hygienic, simple, reliable and/or reproducible filling of the cartridge—in particular without spillage—is achieved or at least facilitated and/or wherein the amount of the fluid and/or a (remaining) gas within the cartridge is precisely and/or reproducibly adjusted/adjustable and/or wherein the amount of the remaining gas within the cartridge is minimized.

SUMMARY

The cartridge according to the present invention preferably comprises a—preferably rigid and/or cylindrical—container, a movable—preferably flexible—fluid piston arranged therein and/or a closure part, in particular a plug, preferably wherein the closure part seals/closes the container, in particular its opening, mostly preferred in a liquid- and/or gas-tight manner.

The container is preferably embodied as a cylinder sleeve.

The closure part is preferably cone-shaped and/or adapted to sealingly receive a connecting element of a nebulizer.

The fluid piston is preferably moved towards the closure part when the cartridge is used/emptied by means of the nebulizer (normal movement of the fluid piston).

Preferably, the closure part, the container and the fluid piston delimit/define a volume that can be varied, in particular reduced, by moving the fluid piston within the container, in particular towards the closure part.

Particularly preferably, the fluid piston forms a (movable) bottom of the cartridge and/or delimits the volume inside the cartridge or container in the axial direction and/or towards the bottom. In particular, an upper axial end face or front portion of the fluid piston faces (directly) the fluid or volume or inside of the container/cartridge and a lower axial end face or back portion of the fluid piston faces (directly) the outside or environment.

The proposed method for producing the cartridge preferably comprises the steps of:
  providing the container, the closure part and the fluid piston,
  arranging the fluid piston in the container,
  filling the fluid, i.e. a pre-defined volume/amount thereof, into the container, in particular via an opening of the container and/or from above, and
  inserting the closure part into the container and/or its opening (at least partially), in particular in order to close/seal the cartridge.

According to one aspect of the present invention, by inserting the closure part at least partially into the container and/or its opening, the pressure within the container is increased and/or the fluid piston is moved/set into motion, in particular downwards, i.e. towards a bottom of the container, and/or away from the closure part and/or such that its (axial) position is changed, i.e. the fluid piston is moved out of its initial/raised position to an end/lowered position.

Due to the fluid piston, in particular its movement during the production of the cartridge, in particular during the sealing/closing of the container by means of the closure part and/or during the insertion step, it is possible to at least partially compensate a pressure increase that occurs during the production of the cartridge, in particular during the sealing/closing of the container by means of the closure part, and/or that is caused by inserting/pressing the closure part into the container. In this way, a fast, simple, hygienic and reliable production/filling is achieved, in particular wherein an unwanted pressure increase is prevented/limited.

Further, the remaining gas, in particular air, within the cartridge can be reduced and/or the amount/volume of the fluid contained in the cartridge can be increased.

Preferably, when the closure part is inserted at least partially into the container or its opening, the pressure within the container increases and, due to the pressure increase, the piston moves, thereby advantageously compensating the pressure increase.

Fluid displaced by the closure part is preferably displaced towards the bottom, in particular into space previously occupied by the piston before its movement. Advantageously, the fluid stays inside of the container and does not spill over and/or is not trapped at the closure part. Thus, advantageously, essentially all of the fluid is available for dispensing, in particular by means of the nebulizer, and/or no fluid is wasted during the production process.

Preferably, after closure, a gas volume remains within the cartridge or container. This is advantageous in order to compensate pressure changes in the cartridge that might be caused by changes in temperature, e.g. during storage and/or transportation of the cartridge. Particularly preferably, the remaining gas volume can be precisely and/or reproducibly adjusted or set by the proposed production method. However, it is also possible that, after closure, no gas volume remains within the cartridge or container.

Preferably, in the arranging step and/or before filling the container and/or before the filling step, the fluid piston is preferably inserted into the (empty) container to an initial/raised position in which the fluid piston is moved closer to the opening of the container and/or comprises a (predefined) offset/distance from the bottom of the container. With other words, in particular in the arranging step and/or before filling the cartridge with the fluid, the volume of the container is intentionally reduced by pushing the fluid piston into the container, preferably until it reaches the initial/raised position.

Preferably, in the initial/raised position, the fluid piston is encompassed by the container along its entire axial extension and/or is completely arranged within the container, in particular with an offset to the bottom or axial end of the container.

Subsequently and/or in the filling step, the fluid, in particular a predefined volume/amount/quantity thereof, is filled into the container, in particular until a first filling level and/or the required fluid volume is reached.

Subsequently and/or in the (first part of the) insertion step, the closure part, in particular its preferably cone-shaped end, is (loosely) inserted into the container, in particular its opening, and/or partially immersed in the fluid, thereby displacing the fluid and/or the gas contained within the container and/or such that the filling level/fluid surface rises. In this way, a second filling level is reached.

Preferably, gas/air contained in the container can escape from the container, when the closure part is inserted into the container and/or in the first part of the insertion step, at least until the closure part closes/seals the container and/or reaches a first position, in which the closure part abuts/closes/seals or starts to seal the container.

With other words, the closure part is preferably loosely inserted without closing/sealing the container and/or without raising the pressure in the container, in particular since a fluid connection between the interior of the container and the exterior is maintained. Thus, the pressure within the container is preferably maintained and/or not increased until the closure part abuts/closes/seals the container and/or reaches the first position.

When the closure part abuts/closes/seals the container for the first time and/or reaches the first position, the first part of the insertion step is preferably completed.

Subsequently and/or in the (second part of the) insertion/sealing step, the closure part is (sealingly) inserted, in particular pressed, further into the container, thereby preferably increasing the sealing surface between the closure part and the container, preferably its inner wall/side, in particular to establish a liquid- and/or gas-tight seal and/or until a second position of the closure part is reached.

Particularly preferably, the sealing is established between the inner wall/side of the container and the outer wall/side of the closure part, in particular the outer diameter of the closure part being greater than the inner diameter of the container in the region of the sealing such that a press/tight-fit of the closure part in the container is established. This is conducive to a particularly good sealing.

Preferably, during the (second part of the) insertion/sealing step and/or by (sealingly) inserting the closure part (further) into the container, the pressure within the container is temporarily increased, preferably since the fluid and, if present, (remaining) gas/air contained in the container cannot escape anymore.

Preferably, during the (second part of the) insertion/sealing step and/or by (sealingly) inserting the closure part (further) into the container the (radial) sealing surface between the closure part and the container is increased.

Preferably, during the (second part of the) insertion/sealing step, by (sealingly) inserting the closure part (further) into the container and/or due to the pressure increase caused in this way, the fluid piston is moved/pushed and/or set in motion, in particular away from the opening and/or the closure part and/or towards the bottom of the container and/or from its initial/raised positon to an end/lowered position. In particular, the offset of the fluid piston from the bottom of the container is at least partially, preferably at least essentially completely, reduced. In this way, pressure increase can be at least partially compensated, as already mentioned.

In the end/lowered position, the lower axial end face or back portion of the fluid piston is preferably at least essentially flush with the axial end of the container.

Preferably, the pressure increase is (almost) instantly compensated by means of the fluid piston movement, in particular depending on the friction between the piston and the container.

Thus and/or as a result, the pressure within the cartridge is at least essentially kept constant and/or corresponds to the ambient pressure during the (entire) production/filling process of the cartridge and/or even when the container is sealed/closed by means of the closure part and/or even when the closure part is sealingly inserted into the container.

The sealing/closing of the container by means of the closure part and/or the insertion step/process of the closure part is preferably done in several, preferably two, steps and/or comprises several, preferably two, stages/parts, in particular wherein the closure part is (loosely) inserted into the container and/or positioned in the opening of the container in a first stage/part, in particular until a radial sealing between the closure part and the container is established for the first time and/or the first position is reached, and subsequently (sealingly and/or further) pressed into container in a second stage/part, in particular until a axial sealing between the closure part and the container is established and/or the second position is reached.

According to the invention, the fluid piston, in particular the movability of the fluid piston, is used during the production of the cartridge to compensate/prevent a pressure increase and/or such that fluid can be displaced towards the piston. In particular, the fluid piston is moved from an initial/raised position to an end/lowered position during the production of the cartridge, in particular when the container is sealed/closed.

With other words, the fluid piston preferably performs a movement during the production/filling of the cartridge that is in the opposite direction, i.e. downwards, than the (normal) movement of the fluid piston, when the cartridge is used/emptied by means of a nebulizer, i.e. upwards.

Subsequently and/or after the insertion step and/or after closing the container, the top portion, in particular the closure part, and/or the bottom portion of the container, is/are sealed, in particular by means of a top seal or cover and/or a base seal, respectively.

Optionally, the closure part is secured to the container, mostly preferred by a securing element crimped thereto.

In this way, the cartridge is produced and ready for use, i.e. the cartridge can be inserted and/or (fluidically) connected to a nebulizing/dispensing device.

In the context of the present invention, the term "cartridge" preferably refers to a device containing a fluid, in particular a pharmaceutical composition, a medicament or the like, preferably wherein the fluid or a dose thereof is to be dispensed to a user.

A cartridge within the meaning of the present invention is preferably adapted to be inserted and/or fluidically connected to a nebulizer or dispensing device, in particular in order to withdraw and/or dispense a dose of the fluid.

Preferably, the volume of the cartridge or a reservoir of the cartridge is reduced every time the fluid or a dose thereof is dispensed. In particular, the cartridge comprises a (rigid) container and a fluid piston movable therein in order to reduce the volume every time the fluid or a dose thereof is dispensed.

Preferably, a nebulizer is used to dispense/nebulize the fluid or a dose thereof. However, any other kind of dispensing device might be used together with the cartridge, e.g. injectors, pens, syringes or the like.

In the context of the present invention, the term "filling level" preferably is the height of the fluid, i.e. its fluid surface, in the cartridge, in particular measured from the bottom or a bottom side of the cartridge or its container. Preferably, the filling level varies during the production of the cartridge, in particular due to the position of the closure part and/or the fluid piston relative to the container. Preferably, the filling level is changed by immersing the closure part into the fluid and/or by moving the fluid piston relative to the container.

All aspects of the present invention mentioned above and in the following can be realized independently of one another and in any combination or order. Further advantages, features, aspects and characteristics of the present invention will become apparent from the claims and the following description of a preferred embodiment with reference to the drawings.

BRIEF DESCRIPTION OF THE DRAWING

In the figures the same reference numbers are used for identical or similar parts, preferably resulting in corresponding or comparable properties and advantages, even if the associated description is not repeated.

DETAILED DESCRIPTION

Figure 1:
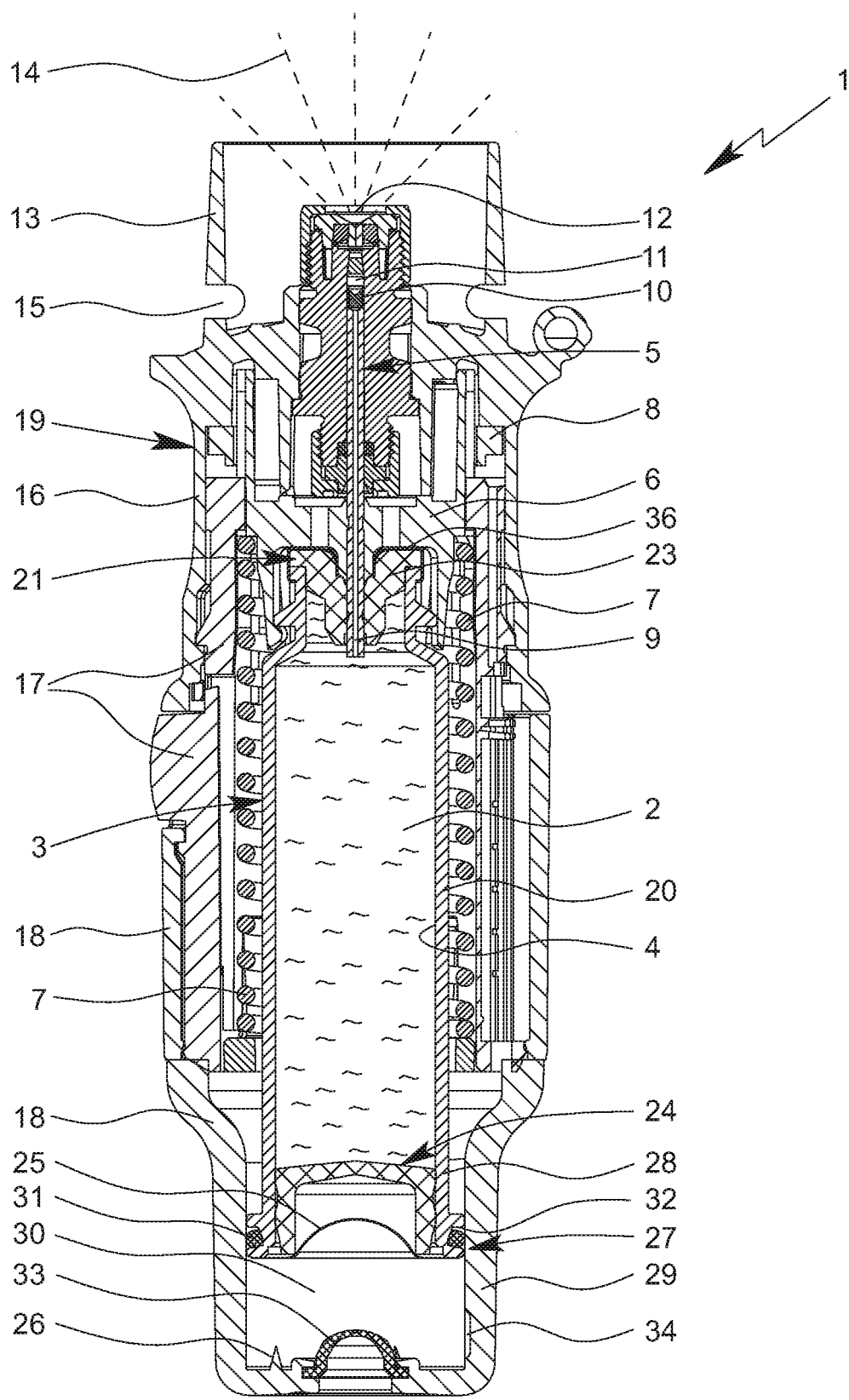
FIG. 1 is a schematic section of a system/nebulizer in a non-tensioned state.
Figure 2:
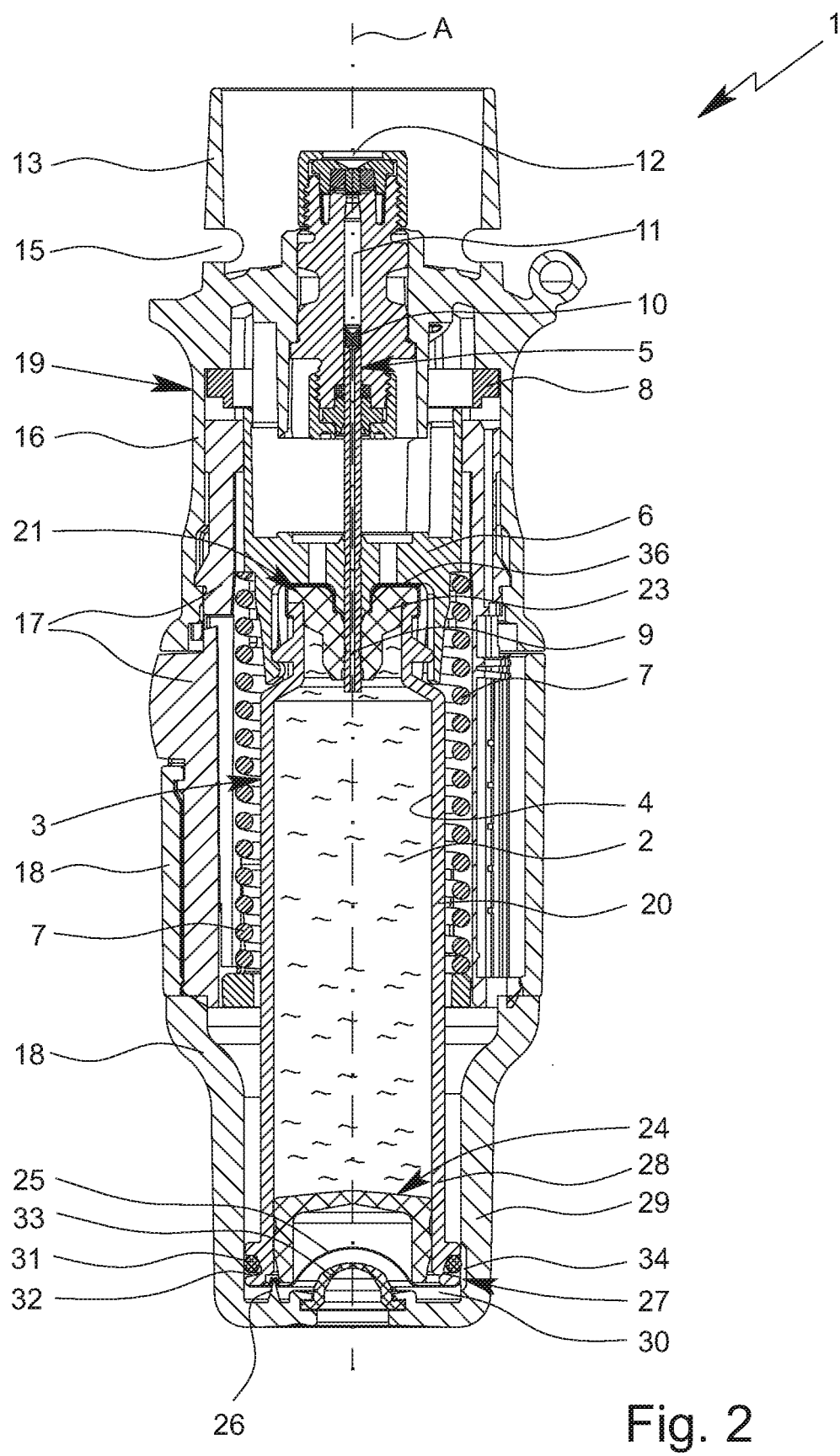
FIG. 2 is a schematic section of the system/nebulizer according to FIG. 1, but in a tensioned state.

FIG. 1 and FIG. 2 show a system/nebulizer 1 for atomizing/nebulizing/dispensing a fluid 2, in particular a pharmaceutical composition, a medicament or the like, schematically shown in a non-tensioned/initial state (FIG. 1) and in a tensioned/ready-to-use/activated state (FIG. 2).

The system preferably comprises the nebulizer 1 and a cartridge 3 containing the fluid 2. With other words, the nebulizer 1 and the cartridge 3 preferably form the system.

The system/nebulizer 1 is preferably adapted to dispense/nebulize the fluid 2 or a dose thereof, in particular in form of an aerosol 14 (as indicated by dashed lines in FIG. 1).

Preferably, the nebulized/dispensed fluid 2 or aerosol 14 can be breathed in or inhaled by a user/patient (not shown).

Usually, the dispensing/inhaling is done at least once a day, preferably several times a day, in particular at set intervals, depending on the complaint/illness from which a patient is suffering.

The system/nebulizer 1 is preferably constructed as a portable inhaler and/or operates preferably only mechanically and/or without a propellant/gas. Nevertheless, other constructions are possible as well.

The nebulizer 1 is preferably adapted to receive the preferably insertable or replaceable cartridge 3, preferably axially and/or from below, as shown in FIGS. 1 and 2.

The cartridge 3 preferably contains the fluid 2 and/or comprises/contains/forms a volume/reservoir 4 for the fluid 2, which is to be nebulized/dispensed, in particular by means of the nebulizer 1.

Preferably, the cartridge 3 contains multiple doses of the fluid 2, in particular sufficient to provide at least 60, 100 or 150 and/or up to 200 or more dosage units or doses, i.e. to allow at least 100 or 150 and/or up to 200 sprays or applications.

The (maximal) volume/reservoir 4 of the cartridge 3 preferably amounts to at least 0.5 ml or 2 ml, in particular at least 4 ml or 6 ml, and/or of at most 100 ml or 50 ml, in particular at most 20 ml or 10 ml.

The number of doses contained in the cartridge 3 and/or the total volume of the fluid 2 contained in the cartridge 3 can vary depending on the fluid 2 or the cartridge 3 and/or on the necessary medication.

Preferably, the nebulizer 1 is adapted to nebulize/dispense a dose of at least 1 µl or 5 µl, in particular at least 10 µl or 15 µl, and/or of at most 100 µl or 80 µl, in particular of at most 60 µl, of fluid 2, when being actuated/used and/or within one actuation/use of the nebulizer 1.

As already mentioned, the cartridge 3 can be replaced or exchanged. With other words, the nebulizer 1 is preferably reusable and/or can be used with a new cartridge 3 once a cartridge 3 is empty.

Optionally, the total number of uses of the nebulizer 1 and/or the number of cartridges 3 which can be used with the same nebulizer 1 is restricted, e.g. to a total number of four, five or six. WO 2012/162305 A1 discloses such a restriction of the total numbers of cartridges 3 which can be used with the same nebulizer 1.

The cartridge 3 preferably comprises a container 20, preferably wherein the container 20 contains the fluid 2 and/or comprises or forms the volume/reservoir 4 containing the fluid 2.

The cartridge 3, in particular the container 20, is preferably at least essentially cylindrical and/or embodied as a hollow cylinder. Mostly preferred, the cartridge 3, in particular the container 20, is at least essentially rotationally symmetric and/or elongated.

Preferably, the nebulizer 1 and/or the cartridge 3, in particular the container 20, comprise/comprises or define/defines an axis A, preferably wherein the axis A is a longitudinal, central, motion and/or rotational axis of the nebulizer 1 and/or the cartridge 3, in particular the container 20. Mostly preferred, the axis A is a common axis of the nebulizer 1 and the cartridge 3.

The axis A preferably runs centrally through the nebulizer 1 and/or cartridge 3, in particular through the container 20 and/or a closure 21 and/or a fluid piston 24 of the cartridge 3.

In the following—if not explicitly stated otherwise—spatial descriptions are preferably made with reference to the axis A, in particular when radial and/or axial alignments or arrangements are specified. Thus, the terms "radial" or "axial" preferably relate to the axis A of the nebulizer 1 and/or cartridge 3.

Preferably, the volume/reservoir 4 for the fluid 2 is variable, in particular collapsible/reducible. In particular, the reservoir/volume 4 is reduced (automatically) when and/or each time a dose of the fluid 2 is withdrawn from the cartridge 3, as will be explained later.

In the present embodiment, the cartridge 3, in particular the container 20, is preferably single-walled. However, other constructional solutions are possible as well, wherein the cartridge 3, in particular its container 20, is multi-walled and/or comprises a flexible/collapsible bag containing the fluid 2.

The cartridge 3 is preferably equipped with a movable element/piston, hereinafter referred to as fluid piston 24, preferably wherein the fluid piston 24 delimits the volume/reservoir 4.

Preferably, the fluid piston 24 is movably arranged/guided within the container 20, in particular in order to reduce the reservoir/volume 4 and/or to prevent any negative pressure (compared to the ambient pressure) caused by the withdrawal of the fluid 2.

The fluid piston 24 preferably closes/seals the cartridge 3, in particular its container 20, axially and/or at its base/bottom, in particular in a gas-tight and/or liquid-tight manner.

The cartridge 3 preferably comprises the closure 21, preferably wherein the closure 21 closes/seals the cartridge 3, in particular its container 20, axially and/or at its top, in particular in a gas-tight and/or liquid-tight manner.

The volume/reservoir 4 is preferably axially limited by means of the closure 21 and the fluid piston 24 and/or radially limited by means of the container 20.

Due to the movable fluid piston 24 and/or due to the compressibility of the volume/reservoir 4, it is not necessary, to equip the volume/reservoir 4 with a ventilation/aeration, e.g. in form of a valve, opening, hole or the like, in order to enable or support withdrawal of the fluid 2 from the container 20. However, constructional solutions are possible as well, wherein the cartridge 3 or container 20 is equipped with such a ventilation/aeration.

The nebulizer 1 preferably comprises a preferably mechanically operated fluid pump 5 for withdrawal, pressurizing, conveying and/or nebulizing/dispensing of the fluid 2, in particular a—preferably preset and/or adjustable—dosage amount thereof.

The fluid pump 5 is preferably adapted to withdraw/suck fluid 2, namely a dose of the fluid 2, from/out of the cartridge 3, in particular its reservoir/volume 4, preferably during a tensioning/loading process of the nebulizer 1 and/or in a first step.

Subsequently, the withdrawn fluid 2 or dose of fluid 2 is or can be dispensed, in particular (first) pressurized and/or (then) nebulized, preferably by means of the fluid pump 5, in particular during a dispensing/nebulizing process of the nebulizer 1 and/or in a second step.

Thus, the normal use of the nebulizer 1 preferably comprises a two-stage procedure, i.e. the tensioning/loading process, in particular in which energy is transferred into an energy store and/or in which a pump/pressure chamber 11 of the nebulizer 1 is filled with fluid 2, and the dispensing/nebulizing process in particular in which fluid 2 is ejected from the pump/pressure chamber 11.

Preferably, the mechanical energy that has been stored during the tensioning process is released during the dispensing process in order to pressurize and/or nebulize the withdrawn fluid 2 or a dose thereof.

Preferably, the nebulizer 1 comprises an energy store 7. In the present embodiment, the energy store 7 is embodied as a drive spring, in particular a spiral spring, preferably wherein the drive spring is at least partially arranged around and/or encompasses the cartridge 3.

The energy store 7 is preferably loaded during the loading/tensioning process. In case the energy store 7 is embodied as a drive spring, the drive spring is preferably tensioned/compressed during the loading/tensioning process. The energy stored in this way is preferably released during the subsequent dispensing/nebulizing process and/or for dispensing/nebulizing the fluid 2 or a dose thereof.

As already mentioned, the nebulizer 1 is preferably adapted to (axially) receive the cartridge 3, mostly preferred in order to establish a fluid connection between the cartridge 3, in particular its volume 4, and the fluid pump 5.

Preferably, the nebulizer 1 comprises a holder 6 for—in particular releasably and/or axially—holding the cartridge 3, in particular its closure 21, and/or in order to establish a mechanical connection between the cartridge 3, in particular its closure 21, and the nebulizer 1.

Preferably, the energy store 7 is associated to and/or (axially) abuts the holder 6. Preferably, the holder 6 is (axially) moved to load the energy store 7 and/or tension the drive spring.

The holder 6 and the fluid pump 5 are preferably mechanically connected to one another. In this way, the energy of the energy store 7 is transferred from the energy store 7 via the holder 6 to the fluid pump 5.

The nebulizer 1 preferably comprises a blocking element 8, preferably wherein the blocking element 8 is adapted to catch and/or block the holder 6 and/or energy store 7 after the loading/tensioning process is completed and/or in such a way that the energy stored during the earlier loading/tensioning process is not unintentionally and/or immediately released.

Preferably, the blocking element 8 is manually actuated in order to release the holder 6 and/or the energy store 7, preferably allowing the energy store 7 to release energy, in particular allowing the compressed drive spring forming the energy store 7 to expand. With other words, the dispensing process is preferably initiated by manually actuating the blocking element 8.

The nebulizer 1, in particular the fluid pump 5, preferably comprises a conveying/connecting element 9, e.g. a conveying tube, a non-return valve 10, a pressure chamber 11, a nozzle 12 and/or a mouthpiece 13.

Preferably, the connecting element 9 fluidically connects the cartridge 3, in particular its volume 4, to the nebulizer 1, in particular the fluid pump 5, when inserting the cartridge 3 into the nebulizer 1.

Thus, by inserting the cartridge 3 into the nebulizer 1, the cartridge 3 is—preferably simultaneously—mechanically connected to the nebulizer 1, in particular by means of the holder 6, and fluidically connected to the nebulizer 1, preferably its fluid pump 5, in particular by means of the connecting element 9.

The connecting element 9 preferably penetrates and/or pierces the closure 21, container 20 and/or volume 4, when inserting the cartridge 3 into the nebulizer 1 and/or connecting the cartridge 3 to the fluid pump 5.

Preferably, the connecting element 9 is constructed as an elongated hollow cylinder and/or as a preferably capillary tube. Mostly preferred, the connecting element 9 is at least essentially coaxial to the axis A.

Preferably, the connecting element 9 is rigid, in particular made out of metal, mostly preferred out of stainless steel, and/or adapted to pierce or break the closure 21 and/or a seal/cover thereof.

Preferably, the connecting element 9 is constructed as a capillary, in particular having an inner diameter of less than 1 mm or 0.8 mm, mostly preferred less than 0.7 mm or 0.5 mm, and/or more than 0.1 mm or 0.2 mm. However, the inner diameter should not be dimensioned to small as this reduces the flow rate that can be achieved within the connecting element 9.

When the energy store 7 is loaded in the loading/tensioning process, the cartridge 3, the holder 6, the connecting element 9 and/or the non-return valve 10 are preferably moved (together) downwards and/or towards the base/bottom of the nebulizer 1.

Due to the movement of the cartridge 3, the holder 6, the connecting element 9 and/or the non-return valve 10, the volume of the pressure chamber 11 is preferably enlarged and/or the pressure within the pressure chamber 11 is decreased, in particular such that the fluid 2 is withdrawn from or sucked out of the cartridge 3 via the connecting element 9 into the fluid pump 5, in particular through the non-return valve 10 into the pressure chamber 11.

In this state and/or at the end of the loading/tensioning process, the holder 6 or energy store 7 is caught by blocking element 8 so that the energy is kept in the energy store 7, in particular so that the drive spring is kept tensioned/compressed, as already mentioned. Subsequently, the nebulizer 1 is in the loaded/tensioned/ready-to-use/activated state.

In the context of the present invention, loading of the energy store 7 is preferably to be understood as (further) compressing the drive spring forming the energy store 7. Thus, energy is preferably stored in the loaded energy store 7 and/or the activated/tensioned/loaded state is preferably a state in which the drive spring is (further) compressed with respect to its non-tensioned/initial state and/or in which the nebulizer 1 can be actuated and/or a dose of the fluid 2 can be dispensed.

The non-tensioned/initial state is preferably the state in which the drive spring is relaxed or less compressed compared to the tensioned/activated state. Mostly preferred, the non-tensioned/initial state is the state (immediately) after actuation of the nebulizer 1 and/or after dispensing a dose of the fluid 2.

Preferably, the energy stored in the energy store 7 is released by (partial) expansion of the drive spring from the compressed/tensioned state into the initial/non-tensioned state. However, also other solutions are possible, for example in which loading of the energy store 7, in particular tensioning of the drive spring, is to be understood as (further) expanding the drive spring with respect to its non-tensioned/initial state and the energy stored in the drive spring is released by (partial) contraction of the drive spring.

During the dispensing/nebulizing process, i.e. after actuating/pressing the blocking element 8, the cartridge 3, the holder 6, the connecting element 9 and/or the (now closed) non-return valve 10 are/is preferably moved (together) towards and/or relatively to the nozzle 12 and/or mouthpiece 13 and/or away from the base/bottom of the nebulizer 1, in FIGS. 1 and 2 upwards, thereby decreasing the volume of the pressure chamber 11.

Due to the now closed non-return valve 10, the fluid 2 or a dose thereof in the pressure chamber 11 is pressurized. Thus, during the dispensing/nebulizing process the non-return valve 10 preferably acts as a ram or piston.

The pressure generated in this way causes the fluid 2 or a dose thereof to flow through the nozzle 12, whereupon it is nebulized/dispensed, preferably in form of the aerosol 14, as indicated by dashed lines in FIG. 1.

Generally, the nebulizer 1 operates with a spring and/or fluid pressure (in the pressure chamber 11) of at least 5 MPa or 10 MPa, in particular of at least 20 MPa, and/or of at most 200 MPa or 150 MPa, mostly preferred of at least essentially 30 MPa.

The fluid 2 is converted into or nebulized as an aerosol 14, the droplets thereof having an aerodynamic diameter of up to 20 μl, preferably of at least 3 μl and/or of at most 10 μl.

The generated jet spray is preferably cone-shaped and/or has an opening angle of at least 20°, preferably at least 60° or 80°, and/or of at most 160°, in particular of at most 120° or 100°.

A user/patient (not shown) can inhale the aerosol 14 generated in this way, preferably while air can be sucked into the mouthpiece 13 through at least one optional air supply opening 15 in the mouthpiece 13.

Preferably, the aerosol 14 is dispensed at the top of the nebulizer 1 and/or in a direction of the axis A, in FIGS. 1 and 2 upwards.

When normally operated, the axis A of the nebulizer 1 or cartridge 3 is preferably aligned at least essentially vertically. However, it is also possible to use/hold the nebulizer 1 in any other position during the tensioning process and/or dispensing process.

The nebulizer 1 preferably comprises a housing 19 with an upper housing part 16, an intermediate/inner housing part 17 and/or a lower housing part 18, preferably wherein the housing parts 16, 17 and 18 are separate components of the housing 19.

The upper housing part 16 and the lower housing part 18 each preferably comprises or forms an axial end of the preferably elongated nebulizer 1. Preferably, the intermediate/inner housing part 17 is arranged between and/or mechanically connects the upper housing part 16 and the lower housing part 18.

The upper housing part 16 preferably comprises or forms the mouthpiece 13, whereas the lower housing part 18 preferably comprises or forms a bottom/base of the nebulizer 1.

The inner housing part 17 and/or lower housing part 18 are/is movable, preferably rotatable, relative to the upper housing part 16 and/or the mouthpiece 13. In particular, the lower housing part 18 is manually rotatable and/or releasably fixed/fitted/held onto the inner housing part 17, preferably by means of a retaining element.

In order to insert and/or replace the cartridge 3, the housing 19, in particular the lower housing part 18, can be opened and/or the lower housing part 18 can be detached from the nebulizer 1, in particular its inner housing part 17.

The lower housing part 18 is preferably cap-like and/or fits around or over a bottom of the cartridge 3. Mostly preferred, the nebulizer 1, in particular its housing 19, encompasses the cartridge 3 completely, i.e. axially and radially. However, other solutions are possible as well, e.g. wherein the cartridge 3 axially protrudes out of the nebulizer 1, in particular its housing 19.

As already mentioned, the nebulizer 1 or energy store 7 is preferably manually tensioned/loaded, in particular by actuation/rotation of an actuation member, preferably by rotation of the lower housing part 18 or any other component relative to the upper housing part 16, preferably carrying with it or driving the inner housing part 17.

The inner housing part 17 preferably acts on a gear/transmission (not shown) to transform the rotation into an axial movement of the cartridge 3, holder 6 and/or connecting element 9. As a result, the energy store 7 is loaded, i.e. the drive spring is tensioned, in the axial direction by means of the gear/transmission formed between the inner housing part 17 and the holder 6.

During the loading/tensioning process, the cartridge 3, holder 6 and/or connecting element 9 are/is moved axially away from the nozzle 12 and/or mouthpiece 13 and/or towards the bottom of the nebulizer 1 until the cartridge 3, holder 6 and/or connecting element 9 occupies/assumes a lower position, as shown in FIG. 2. In this activated/tensioned/loaded state and/or when the cartridge 3 is in the lower position, the energy store 7 is loaded, i.e. the drive spring is under tension, and caught/held by the blocking element 8, as already mentioned.

During the subsequent nebulizing process, which is preferably initiated by actuating/releasing the blocking element 8, e.g. by pressing a button associated thereto (not shown), the cartridge 3, holder 6 and/or connecting element 9 are/is moved back into its original/initial/upper position, as shown in FIG. 1, in particular by (the force of) the energy store 7.

Thus, the cartridge 3, holder 6 and/or connecting element 9 execute/executes a lifting/stroke movement during the tensioning and nebulizing process, preferably along the (motion) axis A.

Optionally, the cartridge 3 might be provided with an (axial) base/bottom seal 25, preferably wherein the base seal 25 covers/seals the cartridge 3, in particular its axial end or base. Mostly preferred, the base seal 25 covers/seals the gap between the fluid piston 24 and the container 20.

The base seal 25 preferably serves as a barrier against contamination, e.g. dust, and/or can be used as a quality seal and/or label and/or might comprise notes or user instructions.

In the present embodiment, the base seal 25 is preferably curved, in particular concavely on a side facing away from the fluid piston 24 and/or convexly on a side facing the fluid piston 24. Mostly preferred, the base seal 25 is at least essentially dome-like. However, other constructional solutions are possible as well.

Preferably, the base seal 25 is attached, in particular bonded, to the bottom/axial end of the cartridge 3, in particular the container 20. Preferably, the base seal 25 is only attached, in particular bonded, to the container 20 and not to the fluid piston 34 such that the fluid piston 34 is freely movable.

The base seal 25 is preferably opened/pierced/cut open when using/tensioning the nebulizer 1 for the first time, as shown in FIG. 2.

The nebulizer 1, in particular the lower housing part 18, preferably comprises an opening device 26 for opening the base seal 25. In particular, the opening device 26 is adapted to pierce/cut open the base seal 25, preferably between the container 20 and the fluid piston 24 and/or such that air can flow through the base seal 25.

Preferably, the opening device 26 comprises at least one opening element, preferably wherein the opening element comprises a sharp and/or tapered tip in order to open, pierce or cut open the base seal 25. Mostly preferred, the opening element is embodied as a spike or set of spikes. However, other constructional solutions are possible as well.

The nebulizer 1 might be equipped with an optional air pump 27, in particular in order to help to move the fluid piston 24 towards the closure 21 and/or in order to pressurize the fluid 2 in the cartridge 3, in particular (only) during withdrawal of a dose of the fluid 2 and/or during the tensioning process.

The air pump 27 preferably comprises an air piston 28, a cylinder 29 cooperating with the air piston 28 and an air chamber 30 formed/limited by the air piston 28 and the cylinder 29. Thus, the air pump 27 comprises or forms a piston/cylinder arrangement for pressurizing the fluid 2 in the cartridge 3 and/or for increasing the air pressure in the air chamber 30, in particular during withdrawal of a dose of the fluid 2 and/or tensioning of the nebulizer 1.

The cylinder 29 is preferably formed by the axial end or lower housing part 18 of the nebulizer 1. However, other constructional solutions are possible as well, in particular wherein the cylinder 29 is formed by an element or insert attached to or arranged in the nebulizer 1, in particular its lower housing part 18.

Preferably, the cartridge 3, in particular its container 20, mostly preferred the axial end thereof, forms or is used as the air piston 28.

The cartridge 3, in particular the container 20, preferably cooperates with the cylinder 29 and/or the lower housing part 18, in particular such that a piston/cylinder arrangement for pressurizing the air in the air chamber 30 and/or the fluid 2 in the cartridge 3 is formed.

Preferably, the volume of the air chamber 30 is defined or varied by the position or movement of the air piston 28 within the cylinder 29 and/or of the cartridge 3 within the nebulizer 1.

Preferably, the air pump 27 acts directly on the fluid piston 24 in order to pressurize the fluid 2 in the volume 4 of the cartridge 3.

Optionally, the cartridge 3 comprises an air seal 31 acting between the air piston 28 and the cylinder 29 and/or arranged between the air piston 28 and the cylinder 29, in particular such that the gap between the air piston 28 and the cylinder 29 is sealed.

Preferably, the air seal 31 is embodied as a sealing ring, i.e. O-ring, in particular arranged on the outside of the cartridge 3 and/or its outer (cylindrical) wall. However, other constructional solutions are possible as well, in particular wherein the air seal 31 is embodied as a sealing lip.

Preferably, the air seal 31 extends around the air piston 28, in particular in a circumferential groove 32 thereof.

Preferably, the air seal 31 comprises/causes a (variable) sealing effect between the air piston 28 and the cylinder 29, preferably wherein the sealing effect depends on the direction of movement of the air piston 28 relative to the cylinder 29.

Preferably, the air seal 31 is adapted to increase the sealing effect, to close the gap between the air piston 28 and the cylinder 29 and/or to seal the air piston 28 against the cylinder 29 during withdrawal of a dose of the fluid 2 from the cartridge 3 and/or during loading/tensioning the nebulizer 1 and/or when the air piston 28 is moved towards the bottom of the housing part 18.

Preferably, the air seal 31 is adapted to decrease the sealing effect, and/or to open the gap between the air piston 28 and the cylinder 29 during pressurizing the dose of the fluid 2 for nebulization and/or during dispensing the dose of the fluid 2 and/or when the air piston 28 is moved towards the mouthpiece 13.

The groove 32 is preferably broader than the air seal 31, in particular such that the air seal 31 is (axially) movable within the groove 32, i.e. up and down.

The groove 32, in particular its width, is preferably tapered and/or comprises preferably a (radial) depth that varies along its axial extension, i.e. along its width.

When the cartridge 3 and/or the air piston 28 is moved downwards, i.e. towards the bottom of the housing part 18 and/or away from the mouthpiece 13, and/or during tensioning/loading of the nebulizer 1, the air seal 31 is preferably moved into the contrary direction within the groove 32, i.e. upwards, and/or into the narrower portion of the groove 32 and/or is pressed with a greater force against the air piston 28/cylinder 29. This increases the force/pressure/friction and/or the sealing effect between the air piston 28 and cylinder 29, in particular such that no air can leak from the air chamber 30 through the gap between the air piston 28 and cylinder 29.

When the cartridge 3 and/or the air piston 8 is moved upwards, i.e. away from the bottom of the housing part 18 and/or towards the mouthpiece 13, and/or during dispensing/nebulizing a dose of the fluid 2, the air seal 31 moves preferably downwards in the groove 32 and/or into its deeper portion. In this way, the air seal 31 is pressed with less force against the air piston 28/cylinder 29. Thus, the force/pressure/friction and/or the sealing effect between the air piston 28 and cylinder 29 is decreased.

In particular, the cartridge 3 can be moved with less frictional resistance during the dispensing/nebulizing process, i.e. due to the variable friction of the air seal 31, it is possible to reduce/minimize the impact of the air pump 27 on the dispensing/nebulizing process.

Preferably, the nebulizer 1, in particular the air pump 27, comprises at least one air valve 33 for controlling or limiting the (maximum) air pressure in the air chamber 30 and/or for aerating the air pump 27 or its air chamber 30 and/or for preventing any underpressure (with respect to the ambient pressure) in the air pump 27 or air chamber 30. However, the air valve 33 is only optional and can be omitted.

In the present embodiment, the air valve 33 is preferably dome-like, curved and/or at least essentially spherical. Mostly preferred, the shape of the base seal 25 matches at least essentially the shape of the air valve 33. In this way, the base seal 25 does not interfere with the air valve 33.

As already mentioned, the base seal 25 is preferably curved, in particular concavely on a side facing the air valve 33.

Preferably, the air valve 33 opens very easily (i.e. at a very low-pressure difference between the ambient pressure and the pressure in the air chamber 30) towards the interior of the air pump 27 and/or air chamber 30 in order to allow ambient air to flow into the air chamber 30 and/or in order to prevent any underpressure in the air chamber 30. With other words, the air valve 33 preferably forms an inlet valve.

Further, the air valve 33 can flex or open to the outside, i.e. away from the interior of the air pump 27, and allows air to escape from the air chamber 30, mostly preferred only if the pressure inside the air chamber 30 is significantly higher than the ambient air pressure, i.e. only if the pressure difference reaches or exceeds a maximum value corresponding to a maximum air pressure. With other words, the air valve 33 preferably additionally forms a control valve.

Optionally, the nebulizer 1, in particular the housing part 18 or air pump 27, comprises a (sterile) filter such that impurities or foreign substances of the air are prevented from entering the air chamber 30. The filter is in particular arranged in the housing part 18 or an opening thereof and/or within or upstream (with regard to air flowing into the pump chamber 30) of air valve 33. Preferably, the filter is embodied as a filter membrane, a perforated plate or a combination thereof.

When the nebulizer 1 is tensioned and/or the cartridge 3 is moved away from the mouthpiece 13 and/or towards the air valve 33, the volume of the air chamber 30 is reduced and the pressure therein is increased (whereas the volume of the pressure chamber 11 is increased and the pressure therein is reduced). In this way, a force is exerted on the fluid piston 24 which helps or supports to move the fluid piston 24 axially and/or to decrease the volume 4. In this way, any underpressure (compared to the ambient pressure) in the volume 4 can be avoided during the withdrawal of a dose of the fluid 2 from the cartridge 3.

Preferably, fluid 2 is pressed/displaced into the fluid pump 5 by means of the fluid piston 34, thus filling the pressure chamber 11.

With other words, due to the air pump 27, a pressure impulse acts on the fluid 2 or volume 4 at the beginning of and/or during the tensioning processing of the nebulizer 1 and/or withdrawal of the fluid 2 from the cartridge 3. This helps withdrawing the fluid 2 in doses from the cartridge 3 without forming any gas bubbles within the cartridge 3.

By means of the air pump 27, it is ensured that the displacement of fluid 2 into the fluid pump 5 remains at least essentially constant for each actuation/use of the nebulizer 1 such that the preferred dose of fluid 2 is dispensed.

Optionally, the nebulizer 1, in particular the air pump 27, comprises a pressure means/depressurization means/pressure relief means 34, hereinafter referred to as pressure relief means 34, preferably wherein the pressure relief means 34 is adapted to control and/or limit the air pressure within the air pump 27 or its air chamber 30, preferably independently of the velocity of tensioning/loading of the nebulizer 1, i.e. independently of the speed which the lower housing part 18 is rotated relative to the upper housing part 16.

Mostly preferred, the pressure relief means 34 is adapted to decrease the pressure in the air pump 27 or its air chamber 30, preferably dependent on the (axial) position of the cartridge 3 within the nebulizer 1 or lower housing part 18.

Preferably, the pressure relief means 34 is embodied as a bypass or a bypass channel which is integrated into the air piston 28 or cylinder 29/lower housing part 18.

Mostly preferred, the pressure relief means 34 is formed by a longitudinal/axial groove within the cylinder 29/lower housing part 18.

The pressure relief means 34 is preferably activated or activatable and/or opened or openable when the pre-defined (axial) position of the air piston 28 within/relative to the cylinder 29 is reached, in particular when the air piston 28 reaches its lower axial (end) position and/or (only) during tensioning of the nebulizer 1, in particular at the end of the tensioning process, as shown in FIG. 2.

Preferably, the pressure relief means 34 is adapted to bypass the air seal 31 and/or to pneumatically connect the air pump 27 or its air chamber 30 to the atmosphere/environment, in particular such that a (remaining) overpressure (compared to the ambient pressure) in the nebulizer 1 or air pump 27, in particular its air chamber 30, can be compensated.

In this way, the air pressure is (abruptly) reduced to ambient pressure, when a pre-defined axial position of the air piston 28 within the cylinder 29 is reached and/or when the tensioning process ends.

Thus, due to the air pump 27 and the pressure relief means 34 only very short pressure impulse is generated in order to support moving the fluid piston 24 during withdrawal of a dose of the fluid 2 and/or the tensioning process.

With other words, the pressure relief means 34 ensures that the air chamber 30 is pressureless/unpressurized after the tensioning process is completed. This prevents a leakage (due to overpressure in the reservoir/volume 4) out of the nebulizer 1, in particular its nozzle 12.

In the following, the cartridge 3, in particular its structure when assembled, will be described with reference to FIGS. 3 to 5. Subsequently, the method for the production/filling of the cartridge 3 will be described with reference to FIGS. 7A to 7G.

FIG. 3 shows the cartridge 3 in a schematic section in the delivery/ready-to-use/unused state, i.e. before being fluidically connected to/inserted into the nebulizer 1.

FIG. 4 is an exploded perspective view of the cartridge 3 according to FIG. 3.

The delivery/unused/initial state of the cartridge 3 is preferably the state of the cartridge 3 in which the cartridge 3 is delivered from a factory.

Mostly preferred, the cartridge 3, in particular its closure 21 and/or base seal 25, are/is intact/unopened/unpierced in the delivery/unused state. Thus, the delivery state is to be understood as the state (immediately) before the cartridge 3 is connected to or inserted into the nebulizer 1.

As already mentioned, the cartridge 3, in particular the container 20, is of rigid construction. Preferably, the container 20 is formed integrally and/or as one piece. Mostly preferred, the container 20 is made of glass, metal or hard plastic, in particular cyclic olefin polymers.

Preferably, the cartridge 3, in particular the container 20, is bottle-like and/or shaped as a bottle.

The cartridge 3, in particular the container 20, preferably comprises a length/height of at least 2 cm or 3 cm, in particular 4 cm, and/or of at most 20 cm or 15 cm, in particular of at most 10 cm. Mostly preferred, the cartridge 3, in particular the container 20, comprises a length/height of at least essentially 5 cm.

The container 20 preferably comprises a bottom/base portion 20A, a main portion 20B and/or a top/head portion 20C, preferably wherein the main portion 20B is arranged between the bottom portion 20A and the top portion 20C and/or wherein the bottom portion 20A and the top portion 20C each comprises or forms an axial end of the preferably elongated container 20.

Preferably, the bottom portion 20A forms the air piston 28 of the air pump 27, once the cartridge 3 is inserted into the nebulizer 1.

In particular, the bottom portion 20A of the container 20 is adapted to interact with the lower housing part 18 of the nebulizer 1 in order to form the air pump 27, as already mentioned.

The air seal 31 is preferably attached to the bottom portion 20A. To this end, the bottom portion 20A preferably comprises or forms the groove 32 for the air seal 31.

The bottom portion 20A preferably comprises a bottom side 20D, preferably wherein the bottom side 20D is at least essentially perpendicular to the axis A and/or faces away from the volume 4 and/or faces towards the opening device 26, when the cartridge 3 is inserted into the nebulizer 1.

The container 20, in particular the bottom portion 20A and/or bottom side 20D, preferably comprises or forms a bearing/contact surface for the base seal 25, which is preferably attached, in particular adhered, thereto.

The bottom portion 20A and/or the main portion 20B preferably comprise/comprises an inner diameter and/or an outer diameter, preferably wherein the inner diameter and/or outer diameter are/is at least essentially constant along the axis A.

Preferably, the cartridge 3, in particular the container 20, mostly preferred its bottom portion 20A and/or main portion 20B, comprises an inner diameter of at least 0.5 cm or 1 cm and/or of at most 4 cm or 3 cm, in particular of at least essentially 1.5 cm.

The container 20, in particular the bottom portion 20A and/or main portion 20B and/or the inner surface thereof, preferably comprise/comprises or form/forms a sliding/gliding surface for the fluid piston 24.

Mostly preferred, the fluid piston 24 is in direct contact with and/or radially abuts the container 20, in particular its bottom portion 20A and/or main portion 20B and/or the inner surface thereof. With other words, the container 20, in particular its bottom portion 20A and/or main portion 20B and/or inner surface thereof, radially bears/guides the fluid piston 24.

The fluid piston 24 is preferably arranged within the container 20, in particular its bottom portion 20A and/or main portion 20B, and can move within the container 20, in particular its bottom portion 20A and/or main portion 20B and/or from the bottom portion 20A to the top portion 20C, in particular in order to reduce the volume 4, as already explained.

The fluid piston 24 is preferably at least essentially cylindrical and/or rotationally symmetric.

The fluid piston 24 is preferably formed as one piece and/or integrally. Preferably, the fluid piston 24 is made of plastics, in particular of elastomer, thermoplastic and/or thermoset, mostly preferred of (synthetic) rubber, such as butyl rubber.

Preferably, the fluid piston 24 is embodied as a cap and/or comprises an upper axial end face or front portion 24A, a side portion 24B and/or an optional recess 24C, preferably wherein the recess 24C is arranged on a side facing away from the volume 4 and/or enables the required flexibility of the fluid piston 24.

Preferably, the upper axial end face or front portion 24A faces towards the volume 4, the closure 21 and/or the top portion 20C of the container 20. Mostly preferred, the upper axial end face or front portion 24A is in direct contact with the fluid 2.

The side portion 24B preferably faces and/or is in direct contact and/or radially abuts the container 20, in particular the bottom portion 20A and/or main portion 20B and/or inner surface thereof.

Preferably, the cartridge 3, in particular the fluid piston 24, is provided with at least one circumferential fluid seal 24D acting between the fluid piston 24, in particular its side portion 24B, and the container 20, in particular the bottom portion 20A and/or main portion 20B and/or inner surface thereof. In the present embodiment, the cartridge 3, in particular the fluid piston 24, comprises several, here two, fluid seals 24D, preferably wherein the fluid seals 24D are axially spaced apart from one another. In this way, a reliable sealing between the container 20 and the fluid piston 24 is achieved.

Preferably, the side portion 24B comprises or forms the fluid seal(s) 24D. Thus, the fluid piston 24, in particular the side portion 24B, and the fluid seal(s) 24D are preferably formed integrally. However, other constructional solutions are possible as well, in particular wherein the fluid seal(s) 24D is formed as a sealing ring or sealing lip and/or is held by the fluid piston 24 and/or a groove therein.

Preferably, the (largest) outer diameter of the fluid piston 24, i.e. the outer diameter at the fluid seal 24D, corresponds at least essentially to the inner diameter of the container 20, in particular its bottom portion 20A and/or main portion 20B. Mostly preferred, the outer diameter of the fluid piston 24 is (slightly) larger, e.g. by more than 0.1 mm or 0.5 mm, than the inner diameter of the container 20, in particular the bottom portion 20A and/or main portion 20B, in particular such that the fluid piston 24 is press-fitted into the container 20 and/or radially presses against the container 20, in particular its bottom portion 20A and/or main portion 20B. In this way, it is prevented that the fluid 2 leaks between the fluid piston 24 and the container 20. Due to the frictional force between the fluid piston 24 and the container 20, the fluid piston 24 holds its position within the container 20 and/or an unintentional movement of the fluid piston 24 is prevented.

Figure 3:
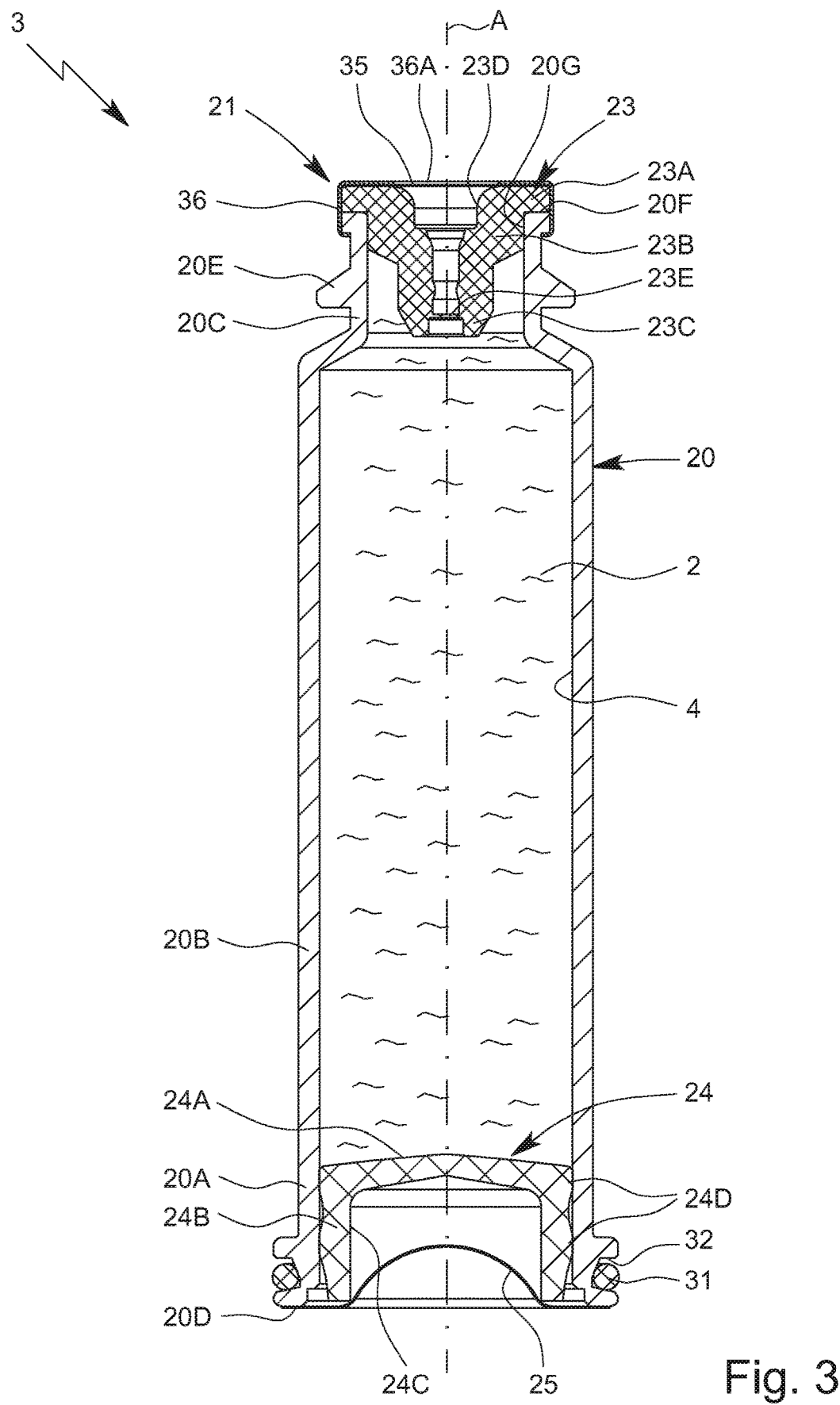
FIG. 3 is a schematic section of a cartridge.
Figure 4:
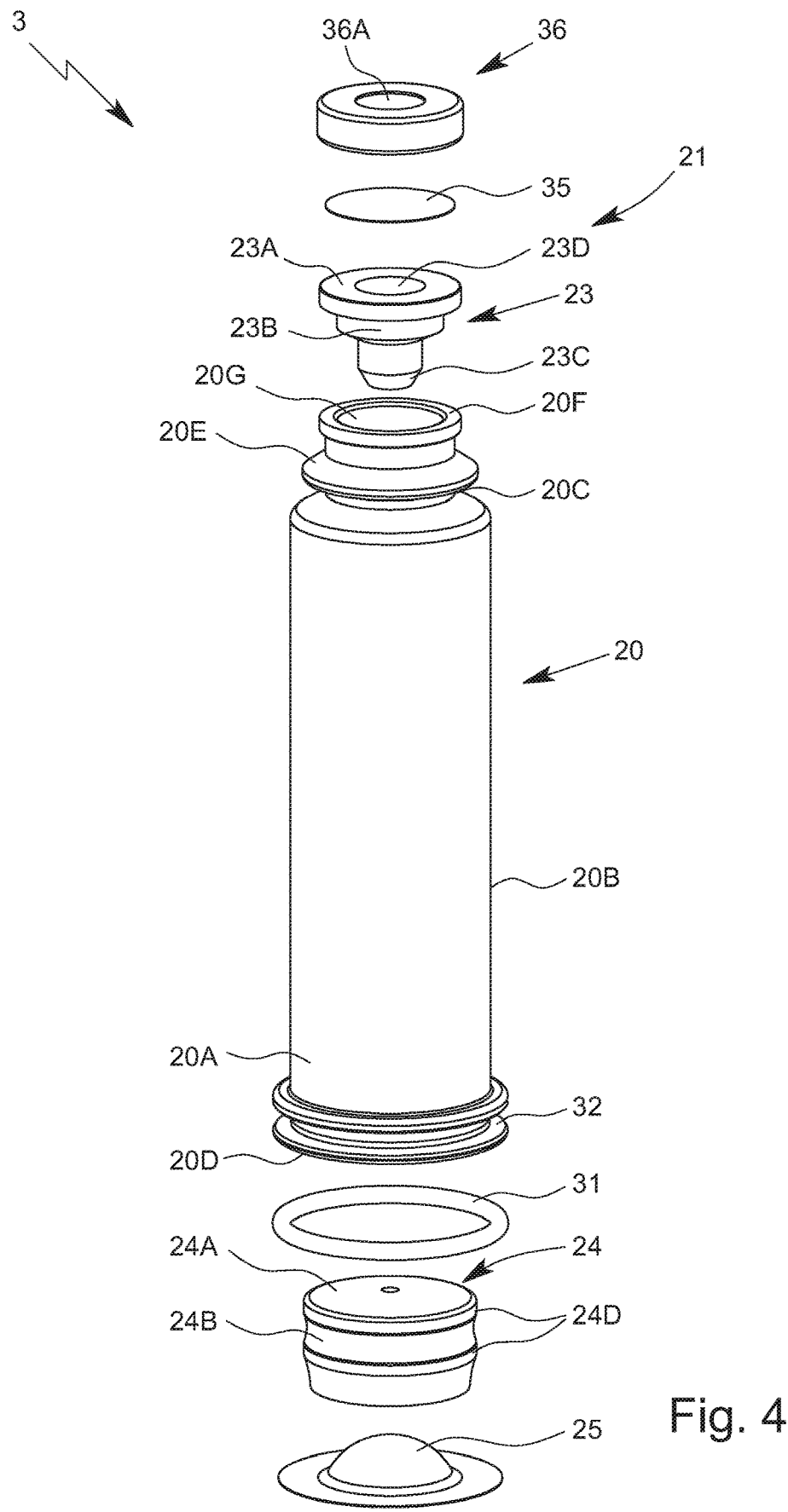
FIG. 4 is schematic exploded view of the cartridge according to FIG. 3.

As already mentioned, the fluid piston 24 preferably comprises an optional recess 24C, in particular facing downwards and/or towards the base seal 25. Mostly preferred, the fluid piston 24, in particular its recess 24C, is adapted to at least partially receive the preferably dome-shaped base seal 25, at least when being in its lower position, as shown in FIG. 3.

Preferably, the fluid piston 24 is completely arranged within the container 20 and/or encompassed by the container 20, in particular along the entire axial extension of the fluid piston 24 or side portion 24B. In particular, no part of the fluid piston 24 protrudes in the axial direction out of the container 20.

Figure 5:
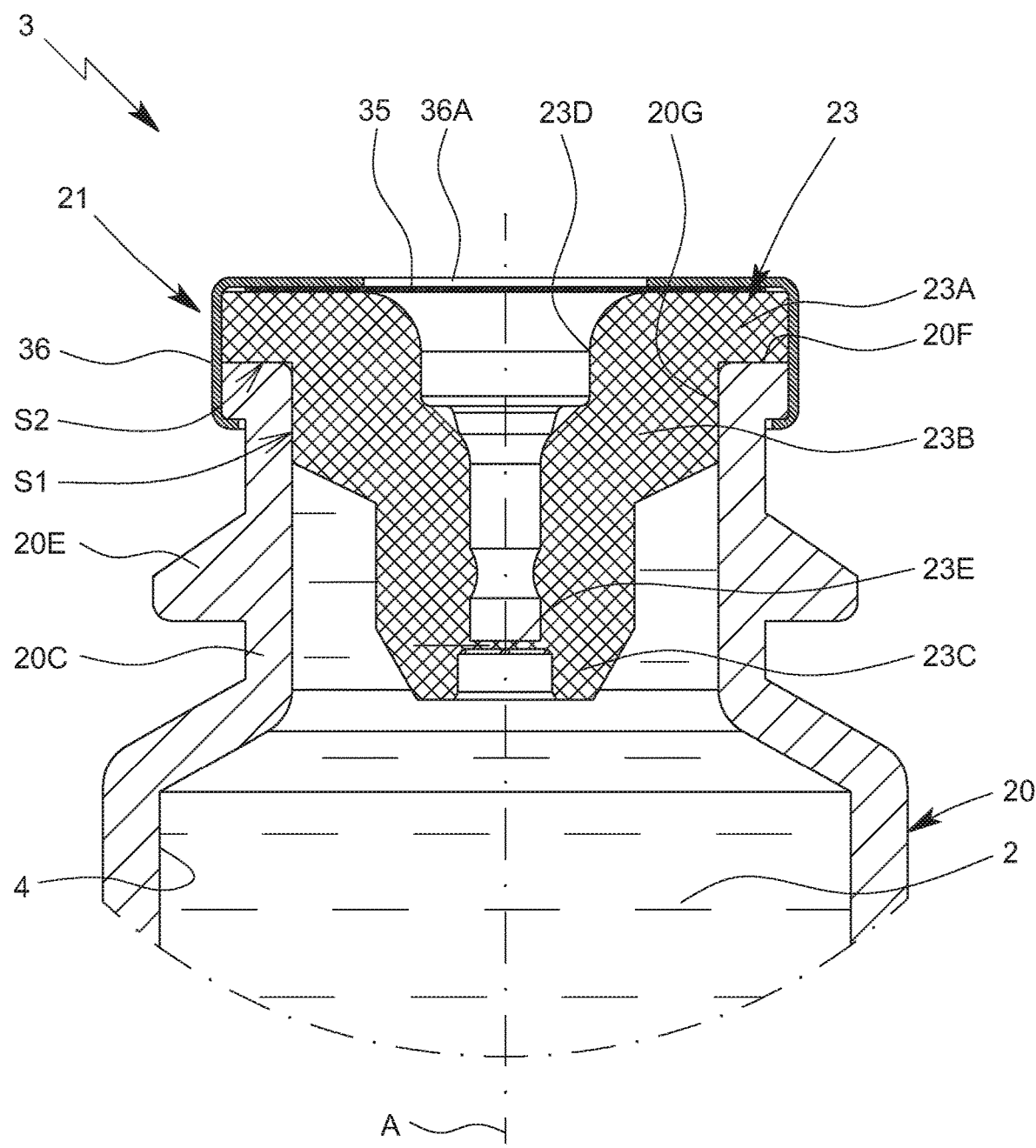
FIG. 5 is a schematic section of the cartridge according to FIG. 3 in the region of its closure.

FIG. 5 shows a detail of the cartridge 3 according to FIG. 3 in the region of the closure 21 and top portion 20C of the container 20 and will be used in the following to describe the upper part of the cartridge 3.

The top portion 20C of the container 20 preferably comprises or forms an axial end of the container 20.

The top portion 20C of the container 20 is preferably narrower and/or has a smaller outer diameter than the bottom portion 20A and/or main portion 20B. Preferably, the top portion 20C comprises or forms a bottle neck of the preferably bottle-like container 20.

Preferably, the inner diameter of the top portion 20C is smaller than the inner diameter of the bottom portion 20A and/or main portion 20B. However, other constructional solutions are possible as well, in particular wherein the container 20 comprises a constant inner diameter along its entire length.

The container 20, in particular its top portion 20C, is preferably used to mechanically connect the cartridge 3 to the nebulizer 1, in particular its holder 6. To this end, the container 20, in particular its top portion 20C, preferably comprises or forms a preferably circumferential connection part 20E.

In the present embodiment, the connection part 20E is embodied as a collar extending radially outward, in particular such that the holder 6 can engage the connection part 20E and axially hold the cartridge 3. However, other constructional solutions are possible as well, in particular wherein the connection part 20E is embodied as a preferably circumferential recess extending radially inward.

The container 20, in particular its top portion 20C, preferably comprises a top side 20F, preferably wherein the top side 20F faces away from the volume 4 and/or faces the holder 6, when the cartridge 3 is connected thereto.

Preferably, the container 20, in particular its top portion 20C, is adapted to at least partially receive the closure 21.

Preferably, the container 20, in particular its top portion 20C, comprises a preferably circular opening 20G, preferably wherein the closure 21 closes/seals the opening 20G and/or is at least partially inserted into the opening 20G.

The cartridge 3, in particular its closure 21, preferably comprises a closure part/plug 23, preferably wherein the closure part 23 is at least partially inserted into the container 20, in particular its top portion 20C and/or opening 20G.

In particular, the closure part 23 (axially) extends into the interior of the container 20, in particular its top portion 20C, and/or into the volume 4.

Preferably, the closure part 23 is formed integrally and/or as one piece.

Mostly preferred, the closure part 23 is flexible/elastic and/or made of a flexible/elastic material, in particular a rubber, an elastomer and/or a plastic with elastomeric properties, such as polyamide, polyethylene, polypropylene, polyurethane, polybutylene terephthalate, polyether block amide, nitrile rubber, butadiene rubber, styrene-butadiene rubber, isoprene rubber, styrene-isoprene rubber, butyl rubber, ethylene propylene diene monomer rubber or the like. Mostly preferred, the closure part 23 is made of butyl rubber. Other suitable materials might be used as well.

Preferably, the closure 21, in particular the closure part 23, is adapted to seal/close the cartridge 3, in particular the container 20, preferably in a gas- and/or liquid-tight manner. Preferably, the closure 21, in particular the closure part 23, is sealingly received/held by/in the container 20, in particular the top portion 20C and/or opening 20G.

Mostly preferred, the closure 21, in particular the closure part 23, is press-fitted into the container 20, in particular the top portion 20C and/or the opening 20G.

Preferably, the closure 21, in particular the closure part 23, comprises or forms at least one preferably integrated seal, in particular to seal the gap between the container 20, in particular the top portion 20C, and the closure 21, in particular the closure part 23.

Mostly preferred, at least one sealing S1, S2 is formed between the preferably rigid container 20, in particular its top portion 20C, and the preferably flexible or deformable closure part 23.

Preferably, a (radial) sealing S1 is formed/established between the closure 21, in particular the closure part 23, and the container 20, in particular its top portion 20C.

Particularly preferably, the sealing S1 is formed/established between the inner wall/side of the container 20, in particular its top portion 20C, and the outer wall/side of the closure part 23, in particular by press/tight-fitting the closure part 23 into the container 20.

Additionally or alternatively, an (axial) sealing S2 is formed/established between the closure 21, in particular the closure part 23, and the container 20, in particular its top portion 20C or top side 20F.

Thus, preferably at least two sealings S1, S2 are provided by (inserting) the closure part 23, in particular wherein the sealings S1, S2 take effect and/or seal in different directions, namely at least essentially axially and at least essentially radially.

The closure part 23 is preferably at least essentially cylindrical and/or rotationally symmetric.

Preferably, the closure part 23 is tapered and/or in particular stepwise cone-shaped, in particular towards the interior of the container 20, and/or comprises a decreasing outer diameter, in particular in the direction of the interior of the container 20.

Mostly preferred, the closure part 23 is stepped and/or comprises several, here three, stairs or cone/cylinder portions. However, it is also possible that the outer diameter is at least essentially constant or varies steadily.

The closure part 23 preferably comprises an outer/flange portion 23A, an intermediate/sealing portion 23B and/or an end/tapered portion 23C, preferably wherein the intermediate portion 23B is arranged between the outer portion 23A and the end portion 23C and/or wherein the outer portion 23A and the end portion 23C each comprises or forms an axial end of the closure part 23.

The outer portion 23A is preferably arranged on a side facing away from the interior of the container 20, whereas the end portion 23C is preferably arranged on a side facing the interior of the container 20.

The outer diameter of the outer portion 23A is preferably larger than the outer diameter of the intermediate portion 23B and/or the outer diameter of the end portion 23C.

Preferably, the outer diameter of the outer portion 23A is larger than the inner diameter of the top portion 20C and/or the inner diameter of the opening 20G of the container 20.

The outer portion 23A is preferably flange-like and/or abuts axially the container 20, in particular its top portion 20C and/or top side 20F, thereby preferably forming the (axial) sealing S2.

Preferably, the outer portion 23A comprises of forms a stop, in particular such that the closure part 23 can only be inserted into the container 20, in particular its top portion 20C, until the outer portion 23A abuts the top portion 20C and/or the top side 20F of the container 20.

With other words, the outer portion 23A is preferably the portion of the closure part 23 that extends/protrudes out of the container 20, in particular its top portion 20C. However, other constructional solutions are possible as well, in particular wherein the entire closure part 23 is inserted/arranged in/within the container 20, in particular its top portion 20C.

Preferably, the closure part 23, in particular the intermediate portion 23B, radially interacts with the container 20, in particular the top portion 20C.

Preferably, the closure part 23, in particular its intermediate portion 23B, is press-fitted into the container 20, in particular its top portion 20C and/or opening 20G.

The (radial) sealing S1 is preferably formed between the container 20, in particular its top portion 20C, and the closure part 23, in particular the intermediate portion 23B, mostly preferred in a gas- and/or liquid-tight manner.

The outer diameter of the intermediate portion 23B preferably at least essentially corresponds to the inner diameter of the container 20, in particular its top portion 20C and/or the opening 20G.

Mostly preferred, the outer diameter of intermediate portion 23B is (slightly) larger, e.g. by more than 0.1 mm or 0.5 mm, than the inner diameter of the container 20, in particular the top portion 20C, in particular such that the closure part 23 is press-fitted into the container 20 and/or radially presses against the container 20, in particular its top portion 20C. In this way, the radial sealing S1 is formed/establish and/or it is prevented, that the fluid 2 leaks between the closure part 23 and the container 20.

Preferably, the outer diameter of the end portion 23C is smaller than the outer diameter of the outer portion 23A and/or the outer diameter of the intermediate portion 23B and/or the inner diameter of the top portion 20C of the container 20.

The outer diameter of the end portion 23C is preferably smaller than the inner diameter of the container 20, in particular its top portion 20C, mostly preferred such that a preferably circumferential gap is provided between the end portion 23C and the container 20, in particular the top portion 20C. With other words, the end portion 23C is preferably (radially) spaced apart from the container 20, in particular its top portion 20C.

In the space/gap between the end portion 23C and the container 20, in particular its top portion 20C, gas/air can accumulate.

Preferably, the transition between the intermediate portion 23B and the end portion 23C is formed by an inclination. The inclination preferably helps to position/insert the closure part 23 into the container 20 and/or preferably pushes gas/air trapped in the cartridge 3 away from the end portion 23 and/or the connecting element 9 and/or towards the container 20, thereby preventing the unintentional withdrawal of gas/air.

The closure part 23 preferably comprises or forms an opening/channel 23D, preferably wherein the opening/channel 23D extends axially through the closure part 23, in particular from the outer portion 23A through the intermediate portion 23B to the end portion 23C.

Preferably, the axis A runs centrally through the closure part 23, in particular its opening 23D.

The closure part 23, in particular its opening 23D, is preferably adapted to receive the connecting element 9, preferably sealingly.

In the delivery state of the cartridge 3, as shown in FIG. 5, the opening 23D is preferably closed, i.e. the cartridge 3 is sealed by means of the closure 21 or closure part 23.

Preferably, the closure 21, in particular its closure part 23, comprises a closure seal 23E, preferably wherein the closure seal 23E is located within the opening 23D and/or seals/closes the cartridge 3, closure 21, closure part 23 and/or opening 23D, in particular in a liquid- and/or gas-tight manner.

In the present embodiment, the closure seal 23E is preferably embodied as a membrane or sealing wall. In particular, the closure seal 23E is at least essentially disc-shaped. However, other constructional solutions are possible as well, e.g. wherein the closure seal 23E is embodied as a spherical seal, a film hinge or the like.

Preferably, the closure seal 23E is integrally formed or formed as one piece with the closure part 23, in particular its end portion 23C.

Preferably, the closure seal 23E is pierceable/breakable, in particular by means of the connecting element 9 when being received by the closure part 23. Thus, the connecting element 9 is preferably adapted to pierce/break the closure seal 23, in particular such that a fluid connection is established between the cartridge 3, in particular its volume 4, and the nebulizer 1, in particular its pump 5.

Preferably, the closure seal 23E comprises at least one recessed portion of reduced thickness, preferably wherein the recessed portion forms a pre-determined breaking point of the closure seal 23E, in particular when being pierced/broken by the connecting element 9. The recessed portion preferably partitions the closure seal 23E into a plurality of flexing portions.

Preferably, the recessed portion is at least essentially cross-like or formed as a cross and/or partitions the closure seal 23E into several, in particular three or four, flexing portions, preferably wherein the flexing portions flex apart when the connecting element 9 is pushed into the cartridge 3, as will be described later with reference to FIG. 6.

In the present embodiment, the closure seal 23E is preferably (axially) spaced apart from the axial end of the end portion 23C, in particular such that the flexing portions do not protrude into the volume 4 when the closure seal 23E is pierced/opened. However, it is also possible that the closure seal 23E is arranged at the axial end of the end portion 23C, thereby preferably preventing that gas/air can accumulated in the region of the closure seal 23E.

Optionally, the cartridge 3, in particular its closure 21, comprises a preferably pierceable cover or top seal 35, preferably wherein the cover 35 covers/seals the container 20 and/or the closure 21, in particular its closure part 23 or the opening 23D thereof, at least before the cartridge 3 is inserted into the nebulizer 1.

Mostly preferred, the cover 35 is a foil or film.

Preferably, the cover 35 covers the closure part 23 axially completely and/or extends around or over the circumference of the closure part 23. Mostly preferred, the cover 35 forms a seal preventing that any fluid 2 can escape at the top of the cartridge 3 or container 20.

In particular, the cover 35 protects the cartridge 3, container 20 and/or fluid 2 from contamination, for example by dust. Preferably, the shelf-life of the cartridge 3 is increased and/or the permeability of the cartridge 3 is decreased by providing the cover 35. In addition, the cover 35 preferably provides a tamper-proof seal or originality seal such that a user can easily see if the cartridge 3 is unopened/sealed.

Preferably, the connecting element 9 of the nebulizer 1 pierces or breaks/opens the cover 35 when the cartridge 3 is inserted into and/or connected to the nebulizer 1, in particular its pump 5.

Optionally, the cartridge 3, in particular its closure 21, comprises a securing element 36, preferably wherein the securing element 36 is provided or adapted to secure, hold, fix and/or press the closure 21, in particular the closure part 23 and/or the cover 35, to and/or against the container 20, in particular its top portion 20C, mostly preferred in the axial direction and/or in a form-fit manner.

The securing element 36 is preferably attached to the axial end of the container 20, in particular its top portion 20C.

Preferably, the securing element 36 is formed/embodied as a cap or cover, in particular covering the closure 21, closure part 23 and/or the cover 35 radially and/or axially. Mostly preferred, the securing element 36 is embodied as a crimp cap.

Preferably, the securing element 36 engages with or reaches below a circumferential flange/edge of the container 20, in particular its top portion 20C.

Preferably, the closure part 23, in particular its outer portion 23A, and the container 20, in particular its top portion 20C, are clamped together by the securing element 36. In this way, the closure 21 or closure part 23 is preferably axially fixed or secured by means of the securing element 36, mostly preferred in a form-fitting manner.

The securing element 36 is preferably made of a material which is more rigid than the closure part 23 and/or which is less rigid than the container 20.

Preferably, the securing element 36 is made out of metal, preferably out of aluminum.

The securing element 36 is preferably at least essentially ring-like and/or comprises a central opening/recess 36A, preferably wherein the recess 36A is positioned and/or dimensioned such that the opening 23D of the closure 21 or closure part 23 is not covered by the securing element 36 and/or such that the opening 23D remains accessible and/or such that the securing element 36 does not interfere with the connecting element 9 when connecting the cartridge 3 to the nebulizer 1.

Preferably, the cover 35 is arranged between the closure part 23 on the one hand and the securing element 36 on the other hand.

The cover 35 is preferably attached to the securing element 36, in particular from below, mostly preferred by welding. In particular, the cover 35 is glued, heat-sealed or heat-welded to the securing element 36.

However, it is also possible that the cover 35 is attached to the closure part 23 additionally or alternatively.

To secure the closure part 23 to the container 20, in particular its top portion 20C, the securing element 36—preferably still embodied as a flat ring—is preferably arranged on the closure 21 or closure part 23, in particular such that the central opening 36A is in the correct position or coaxially aligned with the opening 23D of the closure part 23, and is then crimped onto the container 20, in particular its top portion 20C, thereby securing the closure part 23 to the container 20, in particular in a form-fitting manner.

Figure 6:
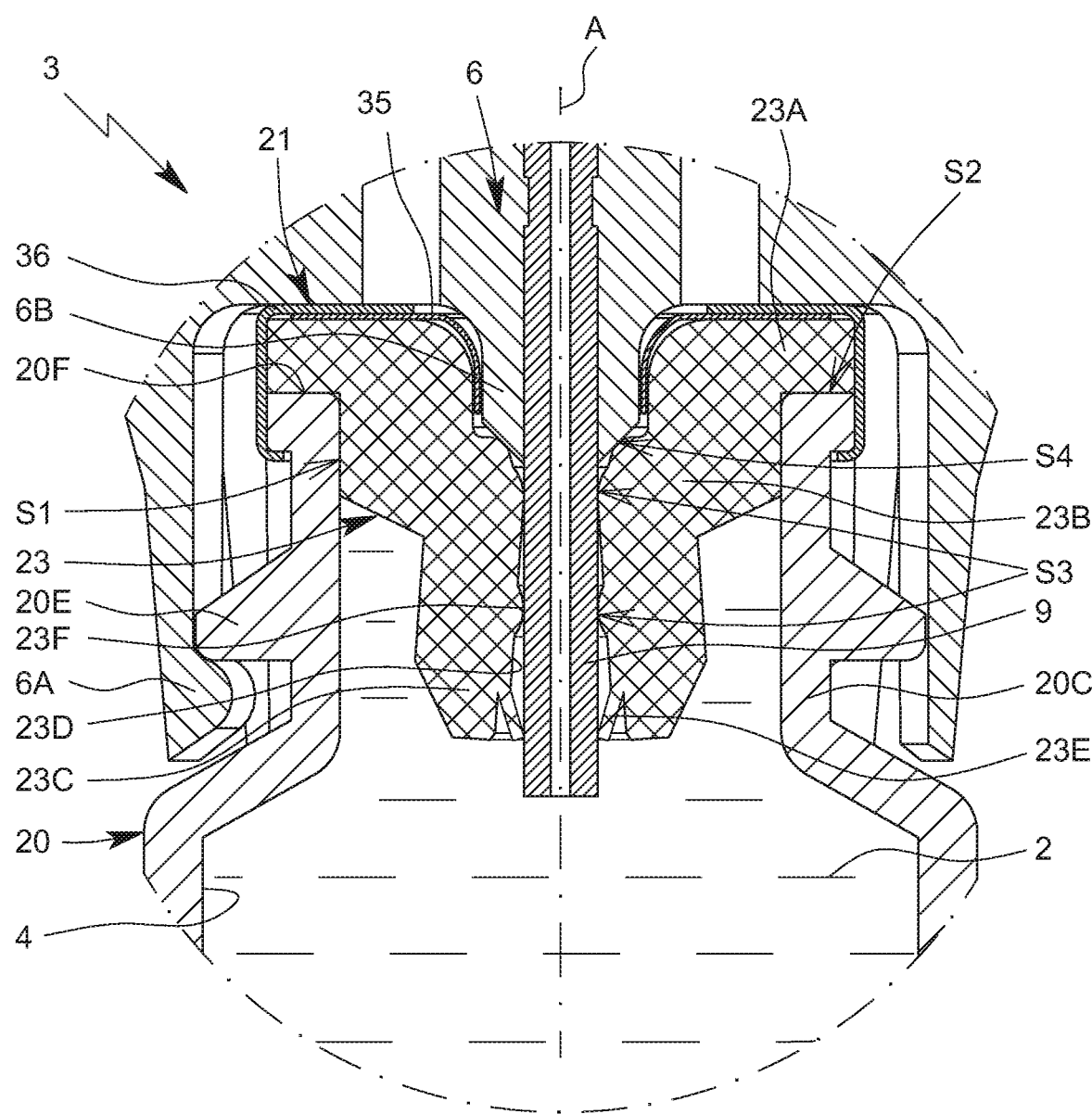
FIG. 6 is a schematic section of the cartridge according to FIG. 5 when being connected to the nebulizer.

FIG. 6 shows the detail of the cartridge 3 corresponding to FIG. 5 when being connected to the nebulizer 1.

As already mentioned, the connecting element 9 of the nebulizer 1 preferably pierces/breaks/opens the cover 35 and/or the closure seal 23E, when the cartridge 3 is inserted into and/or connected to the nebulizer 1, in particular its pump 5.

When the connecting element 9 is pushed against the closure seal 23E, the closure seal 23E preferably tears/breaks/flexes apart, in particular such that the connecting element 9 can pass and penetrate into the volume 4.

Preferably, the flexing portions of the closure seal 23E remain connected to the closure 21, in particular its closure part 23, also after the closure seal 23E has been teared/broken, i.e. after the connecting element 9 has been (completely) inserted.

Preferably, the closure 21, in particular the closure part 23, mostly preferred its end portion 23C, comprises a sealing portion 23F, preferably wherein the sealing portion 23F is formed integrally with the closure part 23, in particular its end portion 23C.

Preferably, the sealing portion 23F is embodied as a circumferential bulge within the opening/channel 23D and/or as a portion of the channel/opening 23D with reduced inner diameter.

In particular, the inner diameter of the sealing portion 23F is smaller than the outer diameter of the connecting element 9.

When the connecting element 9 is received by the closure 21, in particular the closure part 23, the flexible/deformable/stretchable closure part 23, mostly preferred its end portion 23C, is preferably flexed/stretched apart by the connecting element 9, in particular in the region of the sealing portion 23F.

Preferably, in the region of the sealing portion 23F, a preferably tight sealing S3 is formed/established between the connecting element 9 and the closure 21 or closure part 23.

Preferably, also further sealings S3 between the connecting element 9 and the closure 21, in particular closure part 23, are formed/established at other regions, as shown in FIG. 6.

Further, also one or more sealings S4 between the holder 6 and the closure 21, in particular closure part 23, mostly preferred its intermediate portion 23B, can be formed/established.

In this way, a leakage between the connecting element 9 and the closure part 23 is prevented.

In the following the method for producing/filling the cartridge 3 will be described with reference to FIGS. 7A to 7G.

Figure 7A:
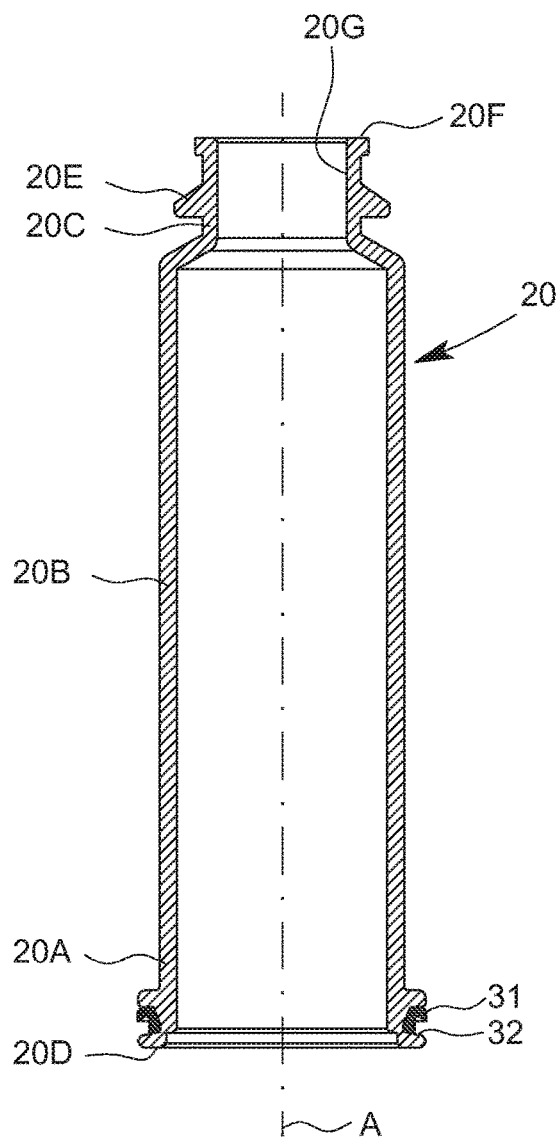
FIG. 7A is a schematic section of an empty container of the cartridge.
Figure 7B:
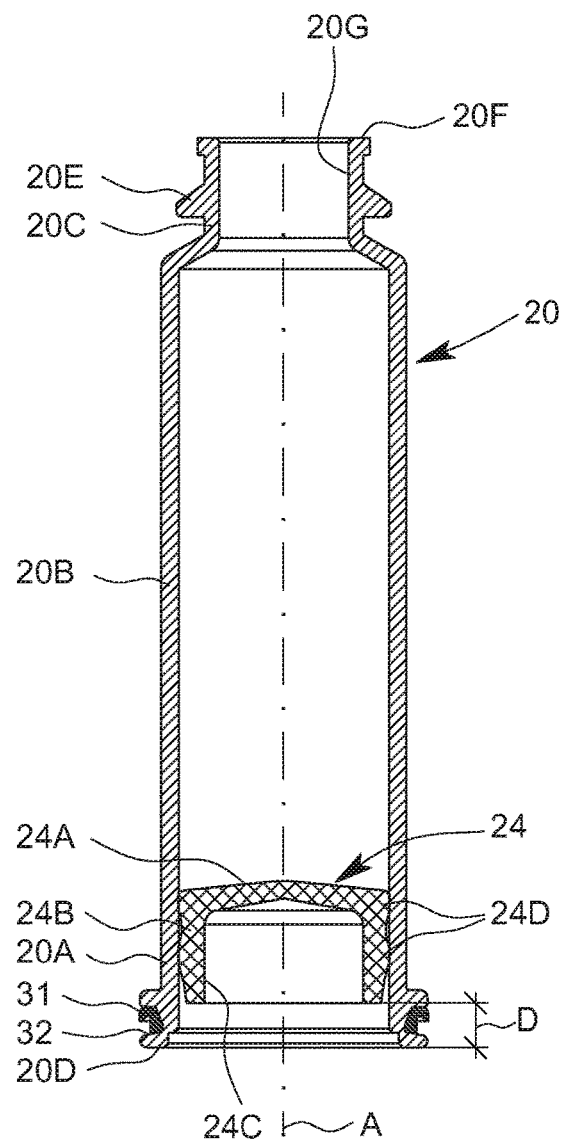
FIG. 7B is a schematic section of the container according to FIG. 7A with an inserted fluid piston.
Figure 7C:
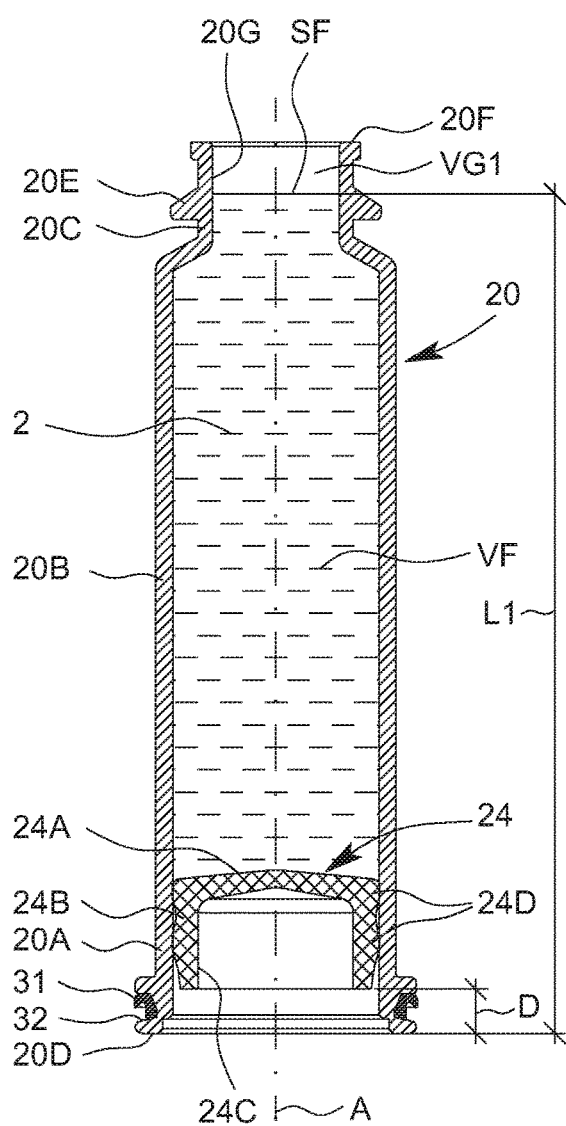
FIG. 7C is a schematic section of the container according to FIG. 7B being filled with a fluid.

FIG. 7A is a schematic section of the (empty) container 20. FIG. 7B is a schematic section of the (empty) container 20 with the inserted fluid piston 24.

Preferably and/or in a first step (shown in FIG. 7A), the container 20 is provided in an empty state. Thus, the container 20 is preferably axially open, in particular on both sides/ends, i.e. its bottom portion 20A and its top portion 20C are open.

Subsequently and/or in a second/next step (shown in FIG. 7B), the fluid piston 24 is inserted and/or press-fitted into the container 20, in particular its bottom portion 20A and/or main portion 20B, mostly preferred from below and/or through its bottom portion 20A. However, it is generally possible to insert the fluid piston 24 from above and/or through the top portion 20C, in particular in case the top portion 20C does not comprise a reduced inner diameter/bottle-neck and/or in case the container 20 comprises a constant inner diameter and/or the inner diameter of the top portion 20C corresponds to the inner diameter of the main portion 20B.

Preferably, the fluid piston 24 is axially spaced apart from the bottom side 20D and/or top side 20F. In particular, the fluid piston 24 is raised/offset from the bottom portion 20A and/or bottom side 20D and/or moved/displaced to the interior of the container 20.

Mostly preferred, the fluid piston 24, in particular its (lowest) axial side (axial side of the side portion 24B) facing towards the bottom side 20D and/or facing away from the top portion 20C, comprises an offset/distance D from the bottom side 20D of the container 20.

In particular, the fluid piston 24 is inserted into the container 20 such that it is in an initial/raised/offset position, as shown in FIG. 7B.

Preferably, the (axial) offset/distance D between the fluid piston 24, in particular its (lowest) axial side facing towards the bottom side 20D and/or facing away from the top portion 20C, and the bottom side 20D of the container 20 is of at least 0.1 mm or 0.5 mm, in particular of at least 1 mm or 2 mm, and/or of at most 10 mm or 7 mm, in the initial/raised/offset position.

The initial/raised/offset position of the fluid piston 24 is preferably the position of the fluid piston 24 relative to and/or within the container 20 immediately before filling the container 20 with the fluid 2 and/or immediately before sealing/closing the container 20 by means of the closure part 23. Preferably, the fluid piston 24 comprises the offset/distance D to the bottom side 20D of the container 20 and/or is spaced apart from the bottom side 20D of the container 20, when being in the initial/raised/offset position.

By insertion of the fluid piston 24, the container 20 is preferably closed/sealed from below, in particular at the bottom portion 20A, particularly preferably by means of the fluid seal(s) 24D.

Subsequently and/or in a third/next step (shown in FIG. 7C), the (empty) container 20 (with its now closed/sealed bottom portion 20A) is at least partially filled with the fluid 2, in particular with a required fluid volume VF, preferably from above and/or through the top portion 20C and/or its opening 20G, in particular until a first filling level L1 and/or the required fluid volume VF is reached.

Of course, it is also possible to offset the fluid piston 24 after the container 20 has been filled with the fluid 2/the fluid volume VF and before the container 20 is closed by means of the closure part 23. In this case, the fluid piston 24 is preferably inserted into the (empty) container 20 in order to axially close the container 20 and the container 20 is subsequently filled with the fluid 2. Thereafter, the fluid piston 24 is pushed further into the container 20 (together with the fluid 2), until the offset/distance D is established and/or the first filling level L1 is reached.

As initially mentioned, the filling level is preferably the height of the fluid 2 in the cartridge 3 and/or the container 20, in particular measured from the bottom side 20D of the cartridge 3/container 20 until the fluid surface. In particular, a filling level corresponds to a particular axial position of the fluid surface SF.

Optionally, the filling of the cartridge 3/container 20 with the fluid 2, in particular the filing level, mostly preferred the first filling level L1, is measured/detected, in particular in a contactless manner and/or by means of a sensor, preferably a level sensor, in particular a conductive level sensor, an ultrasonic level sensor, a capacitance level sensor and/or an optical level sensor.

Preferably, the filling of the cartridge 3/container 20 is stopped when a predefined filling level, in particular the first filling level L1, is reached, mostly preferred automatically.

The first filling level L1 is preferably the filling level immediately after the cartridge 3 and/or the container 20 has been filled with the fluid 2, in particular with the fluid volume VF, and/or (immediately) before the cartridge 3/container 20 is (completely) closed/sealed, in particular by means of the closure 21/closure part 23. Thus, the first filling level L1 is preferably the filling level after the actual filling of the cartridge 3/container 20 has been finished.

Preferably, the container 20 is not filled completely with the fluid 2. With other words, the first filling level L1 preferably does not reach the top side 20F of the container 20.

Preferably, the filling level of the fluid 2 varies during the production of the cartridge 3 (although no further fluid 2 is filled into the cartridge 3 and/or although the fluid volume VF—once in the container 20—is maintained constant during the production of the cartridge 3), in particular due to the position of the closure part 23 and/or the fluid piston 24, as will be explained in the following.

The fluid volume VF is preferably the volume of the fluid 2 in the cartridge 3/container 20, in particular after the filling has been completed and/or before the cartridge 3/container 20 is (completely) closed/sealed, in particular by means of the closure 21/closure part 23.

Preferably, the fluid volume VF is constant during the production of the cartridge 3 and/or once the filling of the cartridge 3/container 20 with the fluid 2 has been completed.

Preferably, the fluid volume VF is of more than 3 ml or 4 ml, in particular more than 5 ml or 7 ml, and/or less than 20 ml or 15 ml, in particular less than 10 ml. Mostly preferred, the fluid volume VF is of at least essentially 8 ml.

Preferably, the volume 4 of the cartridge 3 is larger than the fluid volume VF, in particular such that the cartridge 3 contains a gas volume after the cartridge 3 is filled with the fluid volume VF.

The gas volume is preferably the volume of the gas, in particular between the fluid surface SF and the top side 20F of the container 20, when the filling step is completed and/or when the cartridge 3/container 20 is filled with the fluid volume VF.

Preferably, the gas is air, in particular from the environment. However, any other gas might be used as well during the production of the cartridge 3.

Preferably and/or in contrast to the fluid volume VF, the gas volume varies and/or is reduced during the production of the cartridge 3/container 20 and/or after the cartridge 3/container 20 has been filled with the fluid 2 and/or fluid volume VF, in particular by inserting the closure part 23, as will be explained in the following.

When the cartridge 3/container 20 contains the fluid volume VF and/or when the first filing level L1 is reached and/or immediately before the closure part 23 is inserted, the cartridge 3/container 20 preferably contains a first gas volume VG1.

The first gas volume VG1 is preferably of more than 0.1 ml or 0.2 ml, in particular of more than 0.4 ml, and/or of less than 2 ml or 1 ml.

Preferably, the fluid volume VF is at least 5 or 10 times and/or at most 30 or 20 times larger than the first gas volume VG1.

Subsequently and/or in a fourth/next step (shown in FIGS. 7D to 7F), the cartridge 3/container 20 is closed/sealed, in particular by means of the closure part 23.

The sealing/closing of the container 20 by means of the closure part 23 and/or the insertion step/process of the closure part 23 is preferably done in several, preferably two, steps and/or comprises several, preferably two, stages/parts, in particular wherein the closure part 23 is (loosely) inserted into the container 20 in a first stage/part, in particular until the radial sealing S1 is established for the first time, and subsequently (sealingly) pressed into container 20 in a second stage/part, in particular until the axial sealing S2 is established.

Figure 7D:
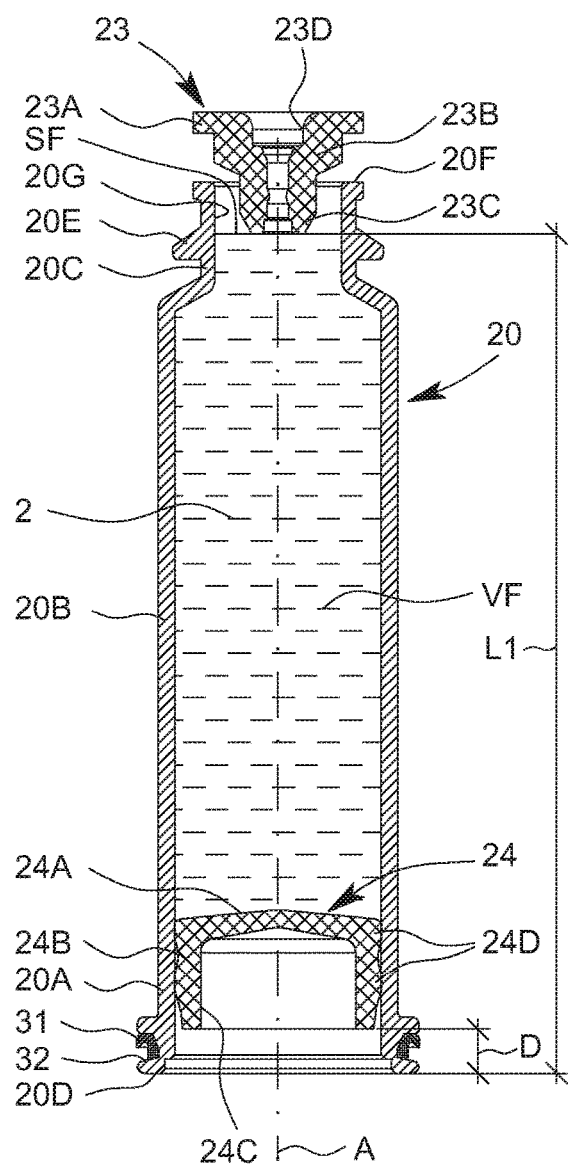
FIG. 7D is a schematic section of the container according to FIG. 7C with a partially inserted closure part, not yet closing the container.

To this end, the closure part 23 is at least partially inserted into the container 20, in particular from above and/or into the top portion 20C and/or into the opening 20G, in particular with the end portion 23C at its insertion front and/or facing towards the fluid piston 24, as shown in FIG. 7D.

The cartridge 3/container 20 is preferably only sealed when the closure part 23, in particular its intermediate portion 23B, (radially) abuts the container 20, in particular its top portion 20C.

FIG. 7D shows the cartridge 3/container 20 with the closure part 23 (loosely) inserted, i.e. at the beginning of (the first part of) the insertion step and/or being in a transition position and/or only partially and/or loosely inserted (not yet sealing/closing the cartridge 3/container 20).

The transition position of the closure part 23 (as shown in FIG. 7D) is preferably the position of the closure part 23 during (the first part of) the insertion step and/or in which the closure part 23 is only loosely inserted into the container 20, in particular its top portion 20C, and/or only the end portion 23C of the closure part 23 is inserted into the container 20, in particular its top portion 20C. Thus, in the transition position, the closure part 23 does not seal/close the container 20, in particular its top portion 20C, and gas contained in the container 20 and/or displaced by means of the end portion 23C can escape, in particular through the gap between the closure part 23, in particular its end portion 23C, and the container 20, in particular its top portion 20C, in particular preferably to the environment.

Figure 7E:
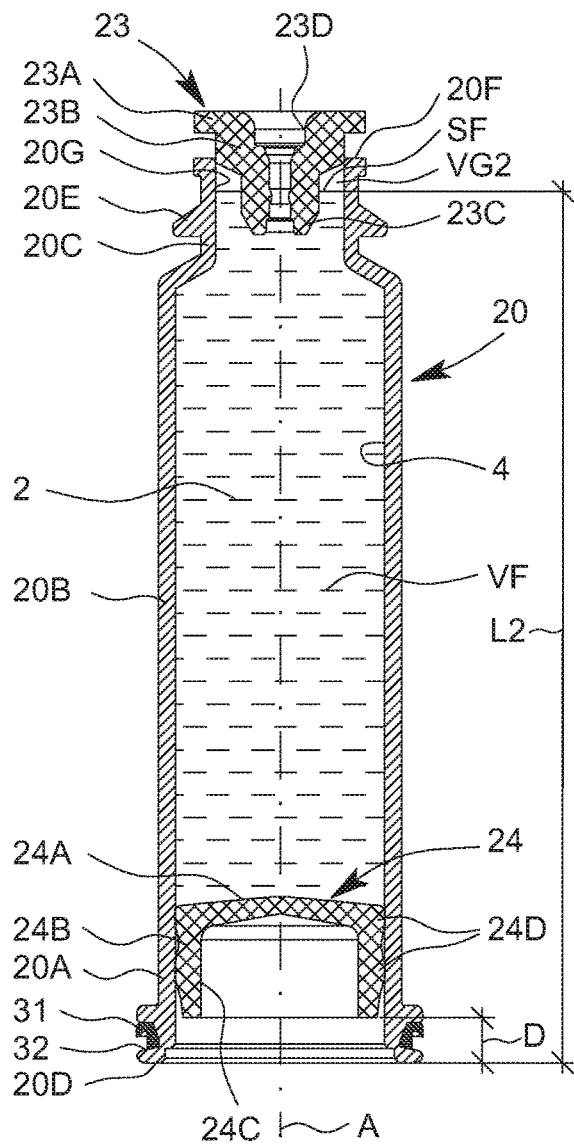
FIG. 7E is a schematic section of the cartridge according to FIG. 7D with the closure part closing the container.

FIG. 7E shows the cartridge 3/container 20 with the closure part 23 in a first/sealing position, i.e. in a position in which the closure part 23 already closes/seals the cartridge 3/container 20 and/or at the end of the first part and/or the beginning of the second part of the insertion step.

The first/sealing position of the closure part 23 (as shown in FIG. 7E) is preferably the position in which the closure part 23, in particular its intermediate portion 23B, (radially) abuts the container 20, in particular its top portion 20C, for the first time and/or such that the closure part 23 (radially) seals/closes the container 20 and/or such that a (remaining) gas contained in the container 20 cannot escape anymore, in particular since the gap between the closure part 23 and the container 20 is now closed and/or the (radial) sealing S1 is established.

In particular by inserting the closure part 23, mostly preferred its end portion 23C, into the container 20, in particular its top portion 20C, gas within the container 20 is displaced and/or pushed out of the cartridge 3/container 20, in particular until the closure part 23 seals the container 20 and/or reaches the first position, as shown in FIG. 7E.

With other words, the gas volume/amount within the cartridge 3/container 20, in particular the first gas volume VG1, is preferably reduced after the cartridge 3/container 20 has been filled with the fluid volume VF and/or by inserting the closure part 23, in particular its end portion 23C, into the container 20, in particular the top portion 20C.

Mostly preferred, the gas volume within the cartridge 3/container 20 is reduced to a second gas volume VG2 when and/or by means of inserting the closure part 23, in particular its end portion 23C, into the container 20, in particular the top portion 20C.

The second gas volume VG2 is preferably the volume of the gas within the cartridge 3/container 20, when the closure part 23 has reached the first position and/or when the cartridge 3/container 20 is sealed/closed, in particular by means of the closure part 23 and/or when the (radial) sealing S1 is established.

Thus, the second gas volume VG2 is preferably the remaining gas volume in the cartridge 3/container 20, i.e. the gas volume that remains after the production of the cartridge 3 is completed.

The second gas volume VG2 is preferably smaller than the first gas volume VG1.

Preferably, the second gas volume VG2 corresponds to less than 80% or 70%, in particular less than 60% or 40%, mostly preferred less than 30% or 20%, and/or more than 1% or 5%, in particular more than 7% or 10%, of the first gas volume VG1.

Preferably, the second gas volume VG2 corresponds to less than 10%, 5% or 1% and/or more than 0.1% or 0.1% of the volume 4 of the container 20 and/or of the fluid volume VF.

The second gas volume VG2 preferably corresponds at least essentially to the volume of a dose of the fluid 2 and/or is preferably of more than 1 µl or 5 µl, in particular of more than 10 µl or 15 µl, and/or of less than 1 ml or 0.5 ml.

Thus, the gas within the cartridge 3/container 20 is preferably reduced to a pre-defined amount/volume during the production of the cartridge 3. In particular, it is also possible to provide a cartridge 3/container 20 with no gas in it at all. However, a remaining gas volume within the cartridge 3/container 20 is also advantageous in order to compensate pressure changes in the cartridge 3, that might be caused by changes in temperature, e.g. during storage and/or transportation of the cartridge 3.

As already mentioned, the fluid level preferably varies during the production of the cartridge 3, in particular after the cartridge 3/container 20 has been filled with the fluid volume VF and/or due to the insertion of the closure part 23 and/or the movable fluid piston 24.

Preferably, the closure part 23, in particular its end portion 23C, is at least partially immersed into the fluid 2, in particular when being inserted into the container 20 and/or even before the closure part 23 seals/closes the container 20, i.e. before the first/sealing position of the closure part 23 is reached.

Preferably, the fluid level at least temporarily rises to a second level L2 when inserting the closure part 23, in particular its end portion 23C, as indicated in FIG. 7E.

The second filling level L2 is preferably higher than the first filling level L1, preferably at least 0.5 mm or 1 mm and/or at most 10 mm or 8 mm.

Preferably, by immersing the closure part 23, in particular its end portion 23C, into the fluid 2, the filling level/fluid surface SF rises, in particular from the first filling level L1 to the second filling level L2, and/or gas within the container 20 is pushed out of the container 20, thereby reducing the gas volume, in particular from the first gas volume VG1 to the second gas volume VG2.

According to a preferred method variant, the filling level/fluid surface SF rises up to the top side 20F of the container 20 and/or the entire gas within the container 20 is displaced/pushed out of the container 20 and/or the second gas volume VG2 equals zero, when the closure part 23, in particular its end portion 23C, is inserted into the container 20 and/or when the closure part 23, in particular its intermediate portion 23B, abuts the container 20, in particular its top portion 20C, and/or when the closure part 23 closes/seals the container 20 and/or reaches its first position.

By immersing the closure part 23, in particular its end portion 23C, into the fluid 2, it is prevented that the connecting element 9 ends in the gas volume VG2 and/or withdraws gas out of the cartridge 3.

Preferably, the fluid piston 24 keeps its (initial/raised) position, once being inserted into the container 20 and/or until the closure part 23 reaches its first position and/or seals/closes/abuts the container 20 and/or during the first part of the insertion step.

Preferably and/or starting from the first position of the closure part 23, the closure part 23 is sealingly and/or further inserted, in particular press-fitted, into the container 20, in particular its top portion 20C, in order to complete the closing/sealing of the cartridge 3/container 20 and/or in order to establish a liquid-tight and/or gas-tight sealing, mostly preferred the (radial) sealing S1 and/or the (axial) sealing S2, between the closure part 23 and the container 20, in particular its top portion 20C, mostly preferred until the outer portion 23A (axially) abuts the container 20, in particular its top portion 20C and/or top side 20F.

Figure 7F:
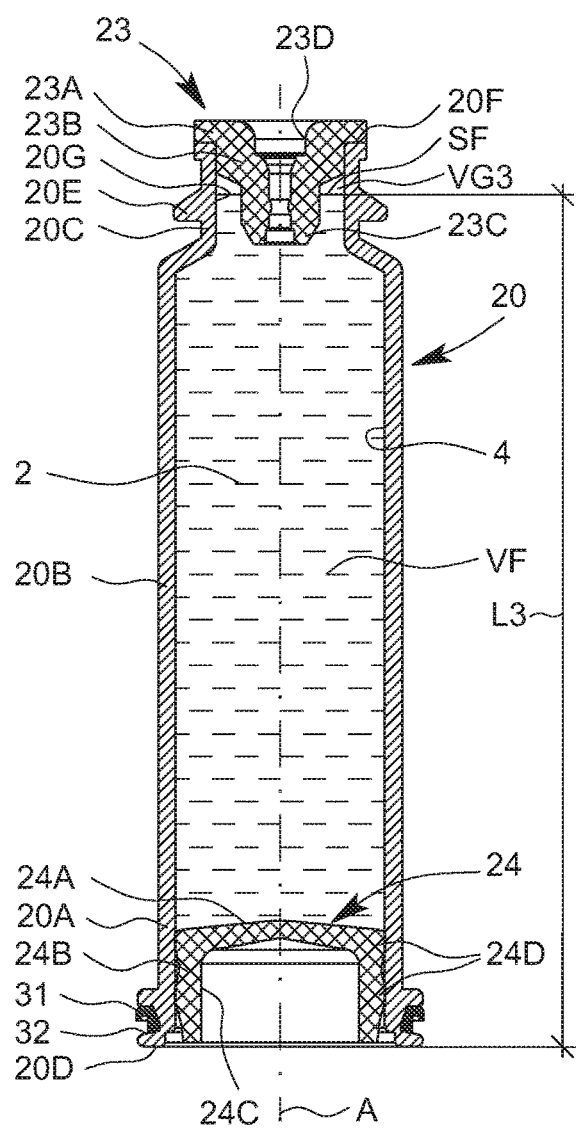
FIG. 7F is a schematic section of the cartridge according to FIG. 7E with completely inserted closure part and the fluid piston being moved downwards.

With other words, the closure part 23 is preferably further inserted into the container 20, in particular its top portion 20C, starting from the first position and/or until reaching a second position and/or until the axial sealing S2 is established, which is schematically shown in FIG. 7F.

The second position of the closure part 23 is preferably the position in which the closure part 23 or its intermediate portion 23B is inserted/pressed completely into the container 20, in particular its top portion 20C, and/or in which the (radial) sealing S1 and the (axial) sealing S2 is established and/or in which the outer portion 23C of the closure part 23 axially abuts the container 20, in particular its top portion 20C and/or top side 20F, and/or in which no further insertion of the closure part 23 into the container 20 is possible.

When moving the closure part 23 from the first position to the second position, the volume 4 of the cartridge 3/container 20 is preferably reduced and/or the pressure in the cartridge 3/container 20 is increased, in particular since the cartridge 3/container 20 is sealed off and/or remaining gas trapped in the cartridge 3/container 20 cannot escape.

According to the invention, the fluid piston 24 is moved—preferably with a stroke that corresponds to the distance D—and/or the position of the fluid piston 24 is changed during the production of the cartridge 3, after the cartridge 3/container 20 has been filled with the fluid 2 and/or fluid volume VF and/or during the second part of the insertion step, in particular in order to compensate the pressure increase caused by sealing/closing the cartridge 3/container 20.

In particular due to the movement of the closure part 23 from the first position into the second position and/or due to the pressure increase, the fluid piston 24 is pushed/moved, in particular away from the closure part 23, the top portion 20C, top side 20F and/or opening 20G and/or towards the bottom portion 20A and/or bottom side 20D of the container 20, in particular such that the pressure increase is at least partially compensated by the movement of the fluid piston 24 and/or by a volume compensation.

Thus, the fluid piston 24 is preferably moved during the production of the cartridge 3 from its initial/raised position to a second/end/lowered position and/or the distance/offset D is preferably reduced, in particular completely and/or such that the fluid piston 24 sits at least essentially flush with the bottom side 20D of the container 20.

The end/lowered position of the fluid piston 24 is preferably the position of the fluid piston 24 when the closure part 23 is in the second position and/or (immediately) after the closure part 23 has reached the second position and/or (immediately) after the closing/sealing of the cartridge 3/container 20 is completed.

Preferably, the fluid piston 24 is further spaced apart from the top portion 20C and/or top side 20F of the container 20 in the end/lowered position compared to its initial/raised position.

Preferably, the distance between the top side 20F of the container 20 and the fluid piston 24, in particular its front portion 24A, in the end/lowered position of the fluid piston 24 is larger than the distance between the top side 20F of the container 20 and the fluid piston 24, in particular its front portion 24A, in the initial/raised position.

Preferably, the offset/distance D between the fluid piston 24 and the bottom side 20D of the container 20 is reduced in the end/lowered position compared to the initial/raised position of the fluid piston 24.

Mostly preferred, the fluid piston 24 sits at least essentially flush with the bottom side 20D of the container 20 in the end/lowered position, i.e. there is preferably no (axial) distance D between the fluid piston 24 and the bottom side 20D.

With other words, the offset/distance D is preferably the difference in the axial position of the fluid piston 24 (immediately) before and after sealing/closing the container 20 by means of the closure part 23.

However, it is also possible, that the fluid piston 24 is still spaced apart from the bottom side 20D of the container 20 when being in the end/lowered position. Of course, it is generally also possible that the fluid piston 24 protrudes axially out of the container 20 in the end/lowered position and/or when being pushed into the end/lowered position.

Preferably, the volume displaced by the closure part 23 when the closure part 23 is moved from its first position to its second position corresponds at least essentially to the volume displaced by the movement of the fluid piston 24 when being moved from its initial/raised position into its end/lowered position. However, the (remaining) gas trapped in the cartridge 3/container 20 might be (slightly) compressed, in particular such that the volume displaced by the closure part 23 might be (slightly) larger than the volume displaced by the fluid piston 24.

Preferably, the fluid 2 is displaced by the closure part 23 at least partially towards the bottom side 20D of the container 20, in particular to the space/volume which becomes available due to the movement of the fluid piston 24.

Particularly preferably, the volume of fluid 2 displaced by the closure part 23 towards the bottom side 20D is at least essentially the volume needed to displace/move the fluid piston 24 by the distance D. In particular, the displaced volume of fluid 2 is at least essentially equal to the distance D times the surface area of the first portion 24A facing the fluid 2.

Since it is preferred that the inner diameter of the head portion 20C of the container 20 is smaller than the inner diameter of the main portion 20B of the container 20, the covered distance of the fluid piston 24 when being moved from its initial position to its end position is preferably smaller than the distance covered by the closure part 23 when being moved from its first position into its second position.

Preferably, the fluid level is changed when the closure part 23 is moved from its first position into its second position and/or the fluid piston 24 is moved from its initial position into its end position, in particular until a third filling level L3 is reached.

The third filling level L3 is preferably the filling level of the fluid 2 when the closure part 23 is in its second position and/or the fluid piston 24 is in its end position. The third fluid level L3 is preferably lower than the first filling level L1 and/or second filling level L2.

Preferably, the (remaining) gas trapped in the cartridge 3/container 20 might be (slightly) compressed, as best seen when comparing FIG. 7E. and FIG. 7F. Thus, when moving the closure part 23 from the first position to the second position, the gas volume might be reduced, in particular from the second gas volume VG2 to a third gas volume VG3 (although the amount/mass of gas is preferably not changed).

This might be caused by a (remaining) overpressure within the cartridge 3/container 20 when the closure part 23 is in its second position and/or the fluid piston 24 is in its end position. This (remaining) overpressure could be caused by a frictional force between the fluid piston 24 and the container 20. However, this overpressure is preferably negligible.

It is also possible that the (remaining) gas is not compressed and/or that the third gas volume VG3 is at least essentially the same as the second gas volume VG2.

As already mentioned, the remaining gas volume in the cartridge 3/container 20, i.e. the second gas volume VG2 and/or the third gas volume VG3, preferably accumulates in the gap/space between the end portion 23C of the closure part 23 and the container 20, mostly preferred in the transition between the end portion 23C and the intermediate portion 23B of the closure part 23 on the one hand and the container 20 on the other hand.

With the proposed method it is possible to control, reduce and/or minimize a (remaining) gas within the cartridge 3 and/or to provide an at least essentially pressure-free cartridge 3, in particular after the production of the cartridge 3 is completed.

Figure 7G:
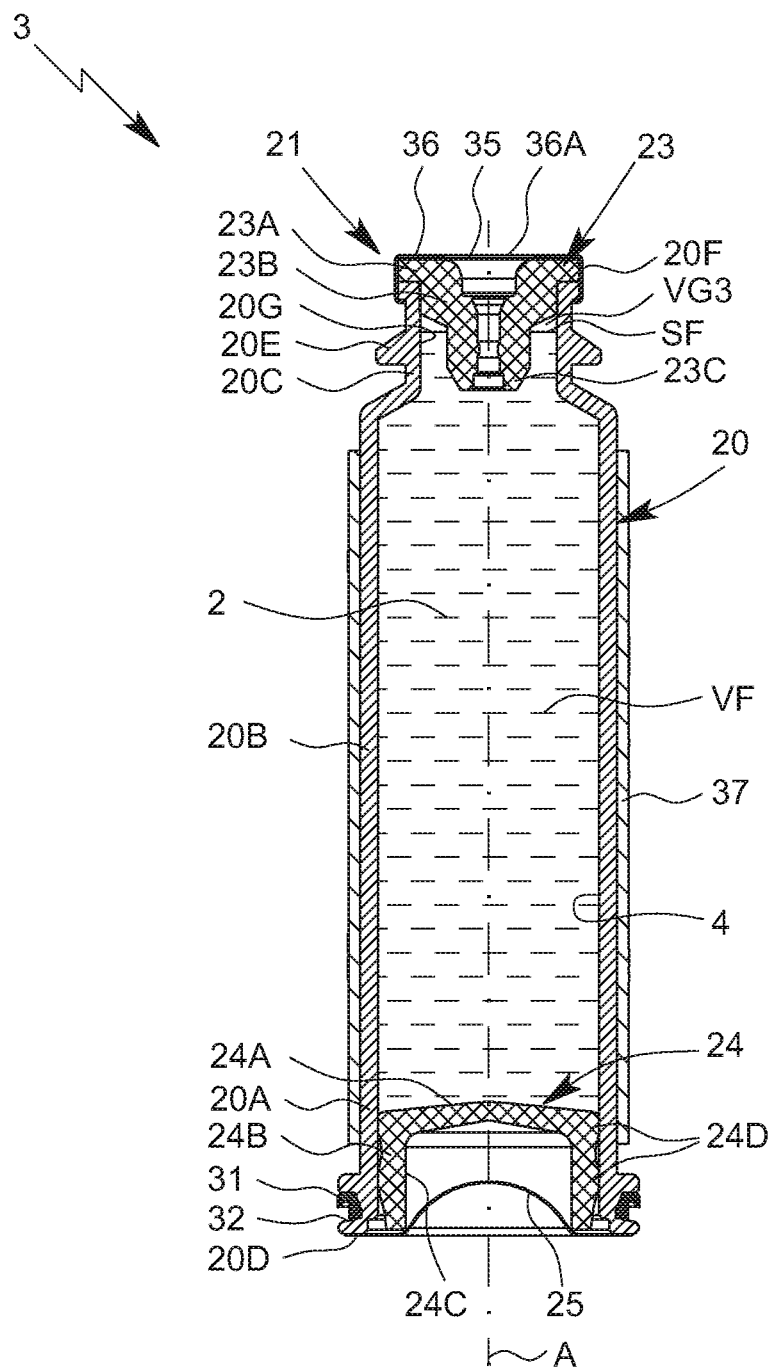
FIG. 7G is a schematic section of the cartridge according to FIG. 7F being sealed and labeled.

Subsequently and/or in a next/fifth step (which is preferably the last step of the method), the container 20, in particular its top portion 20C and/or its bottom portion 20A, is sealed and/or the container 20, in particular its main portion 20B, is labelled, in particular by means of a label 37, as shown in FIG. 7G.

Preferably, the closure part 23 is secured to the container 20, in particular its top portion 20C, in particular by means of the securing element 36 and/or the optional cover 35, as already mentioned.

Preferably, the container 20, in particular its bottom portion 20A, is sealed by means of the base seal 25, which is preferably attached to the container 20, in particular its bottom side 20D.

Preferably, the closure part 23 is secured first, before the base seal 25 is attached, in particular in order to prevent falling off of the closure part 23.

In this way and/or by carrying out one, several or all steps of the described method, the cartridge 3 is produced and/or ready to use, in particular together with the nebulizer 1, as already mentioned.

Individual features, aspects, principles and/or steps described can be realized independently from each other and/or in any combination or order.

The cartridge 3 described herein may not only be used in the nebulizer 1 described herein, but also in other nebulizers, inhalers or other dispensing devices.

Preferred ingredients and/or formulations of the preferably medicinal fluid 2 are listed in particular in WO 2009/115200 A1, in particular on pages 25 to 40, or in EP 2 614 848 A1, paragraphs 0040 to 0087, which are incorporated herewith by reference. Preferably, these ingredients/formulations may be aqueous or non-aqueous solutions, mixtures, formulations containing in particular ethanol and/or being free from any solvent or the like.

| List of reference signs: | |
|---|---|
| 1 | nebulizer |
| 2 | fluid |
| 3 | cartridge |
| 4 | reservoir/volume |
| 5 | fluid pump |
| 6 | holder |
| 7 | energy store |
| 8 | blocking element |
| 9 | connecting element |

-continued

| List of reference signs: | |
|---|---|
| 10 | non-return valve |
| 11 | pressure chamber |
| 12 | nozzle |
| 13 | mouthpiece |
| 14 | aerosol |
| 15 | air supply opening |
| 16 | upper housing part |
| 17 | inner housing part |
| 18 | lower housing part |
| 19 | housing |
| 20 | container |
| 20A | bottom portion |
| 20B | main portion |
| 20C | top portion |
| 20D | bottom side |
| 20E | connection part |
| 20F | top side |
| 20G | opening |
| 21 | closure |
| 23 | closure part |
| 23A | outer portion |
| 23B | intermediate portion |
| 23C | end portion |
| 23D | opening |
| 23E | closure seal |
| 24 | fluid piston |
| 24A | front portion |
| 24B | side portion |
| 24C | recess |
| 24D | fluid seal |
| 25 | base seal |
| 26 | opening device |
| 27 | air pump |
| 28 | air piston |
| 29 | cylinder |
| 30 | air chamber |
| 31 | air seal |
| 32 | groove |
| 33 | air valve |
| 34 | pressure relief means |
| 35 | cover |
| 36 | securing element |
| 36A | opening |
| 37 | label |
| A | axis |
| D | offset/distance |
| L1 | first filling level |
| L2 | second filling level |
| L3 | third filling level |
| S1 | radial sealing |
| S2 | axial sealing |
| S3 | sealing (connecting element - closure part) |
| S4 | sealing (closure part - holder) |
| SF | fluid surface |
| VF | fluid volume |
| VG1 | first gas volume |
| VG2 | second gas volume |
| VG3 | third gas volume |

The invention claimed is:

1. A method for producing a cartridge (3), comprising the steps of:
providing a container (20), which includes engaging elements on at least one of a proximal end and a distal end of the container (20) that are adapted for insertion of the cartridge (3) into, and retaining thereof within, a housing of a dispensing device;
providing a closure part (23) and a fluid piston (24);
arranging the fluid piston (24) in the container (20);
filling a fluid (2) into an opening (20G) of the container (20); and
inserting the closure part (23) into the opening (20G), such that the fluid piston (24) arranged within the container (20) is moved,
wherein at least one of: (i) the closure part comprises an outer/flange portion (23A) and an end/tapered portion (23C), (ii) the outer portion (23A) and the end portion (23C) each comprises or forms an axial end of the closure part (23), (iii) the outer diameter of the outer portion (23A) is larger than the outer diameter of the end portion (23C), (iv) the outer portion (23A) is arranged on a side facing away from the interior of the container (20), and (v) the end portion (23C) is arranged on a side facing the interior of the container (20); and
wherein at least one of: (vi) a radial sealing (S1) is formed between the container (20) and the closure part (23), (vii) the radial sealing (S1) is formed between a top portion (20C) of the container (20) and the closure part (23), (viii) the radial sealing (S1) is formed between the container (20) and an intermediate portion (23B) of the closure part (23), and (ix) the radial sealing (S1) is gas-tight and/or liquid-tight.

2. The method according to claim 1, wherein the fluid piston (24) is initially offset to the bottom side (20D) of the container (20).

3. The method according to claim 1, wherein the fluid (2) is filled into the container (20) until the required fluid volume (VF) and/or a first filling level (L1) is reached, wherein the first filling level is predefined.

4. The method according to claim 3, wherein at least one of:
the filling level is measured/detected by means of a sensor;
the first filling level (L1) is measured/detected by means of a sensor; and
the sensor is at least one of a conductive level sensor, an ultrasonic level sensor, a capacitance level sensor and/or an optical level sensor.

5. The method according to claim 4, wherein at least one of:
the filling of the container (20 is stopped automatically when a predefined filling level is reached, and
the predefined filling level is the first filling level (L1).

6. The method according to claim 1, wherein at least one of: (i) the filling level of the fluid (2) is detected, and (ii) the filling level of the fluid (2) is detected in a contactless manner.

7. The method according to claim 1, wherein at least one of:
the closure part (23) is tapered towards the interior of the container (20);
the closure part (23) is cone-shaped towards the interior of the container (20), and
the closure part (23) comprises a decreasing outer diameter in the direction of the interior of the container (20).

8. The method according to claim 1, wherein at least one of:
the closure part comprises an intermediate/sealing portion (23B),
the intermediate portion (23B) is arranged between the outer portion (23A) and the end portion (23C), and
the outer diameter of the outer portion (23A) is larger than the outer diameter of the intermediate portion (23B).

9. The method according to claim 1, wherein at least one of:
the outer portion (23A) is flange-like and/or abuts axially the container (20), forming an axial sealing (S2); and
the outer portion (23A) includes a top portion (20C) and/or top side (20F) forming an axial sealing (S2).

10. The method according to claim 1, wherein the closure part (23) is partially and/or loosely inserted into the container (20), thereby pushing gas out of the container (20).

11. The method according to claim 10, wherein at least one of:
- the closure part (23) is inserted into the container (20) until the closure part (23) seals the container (20) and/or reaches a first position, in which the closure part (23) radially abuts the container (20), and
- the closure part (23) is inserted into the container (20) until the closure part (23) seals the container (20) and/or reaches a second position, in which the closure part (23) axially abuts the container (20).

12. The method according to claim 11, wherein at least one of:
- the closure part (23), after the first position is reached, is further inserted into the container (20) such that the fluid piston (24) is moved/pushed, and
- the closure part (23), after the first position is reached, is further inserted into the container (20) to a second position, such that the fluid piston (24) is moved/pushed, and
- the second position is such that an axial sealing between the closure part (23) and the container (20) is established and/or the closing/sealing of container (20) is completed.

13. The method according to claim 12, wherein, by further inserting the closure part (23) into the container (20), the fluid piston (24) is moved/pushed away from the opening (20G) of the container (20) and/or towards the bottom side (20D) of the container (20).

14. The method according to claim 10, wherein at least one of:
- the container (20) is sealed by means of the closure part (23) only when or after the second filling level (L2) is reached and/or the closure part (23) is in the first position, and
- the container (20) is sealed, in a liquid-tight and/or gas-tight manner, by means of the closure part (23) only when or after the second filling level (L2) is reached and/or the closure part (23) is in the first position.

15. The method according to claim 1, wherein the closure part (23) is immersed into the fluid (2), thereby displacing fluid (2) and/or gas in the container (20).

16. The method according to claim 15, wherein at least one of:
- the closure part (23) is immersed into the fluid (2) until a second filling level (L2) is reached and/or until the closure part (23) reaches a first position in which it seals the container (20), and
- the closure part (23) is immersed into the fluid (2) until a second filling level (L2) is reached and/or until the closure part (23) reaches a first position in which it radially seals the container (20).

17. The method according to claim 1, wherein gas contained in the container (20) can escape and/or is at least partially or completely pushed out of the container (20) until a second filling level (L2) is reached and/or until the closure part (23) seals the container (20) and/or reaches a first position.

18. The method according to claim 1, wherein less than at least one of: 10%, 5% and 1% of the volume (4) of the container (20) is filled with gas when the closure part (23) seals the container (20) and/or the second filling level (L2) is reached.

19. The method according to claim 1, wherein at least one of:
- the fluid piston (24) is moved away from the opening (20G) of the container (20) and/or towards a bottom side (20D) of the container (20) and/or from an initial position to an end position and/or such that an offset (D) between the fluid piston (24) and the bottom side (20D) is changed, and
- the change is such that such that the offset (D) between the fluid piston (24) and the bottom side (20D) is reduced.

20. The method according to claim 1, wherein a pressure increase caused by sealingly inserting the closure part (23) into the container (20) and/or by moving the closure part (23) from a first position to a second position is at least partially compensated by the movement of the fluid piston (24).

21. The method according to claim 1 wherein at least one of:
- the fluid piston (24) is made of plastics,
- the fluid piston (24) is made of at least one of: elastomer, thermoplastic, thermoset, synthetic rubber, and butyl rubber.

22. The method according to claim 1, wherein the container (20) has an inner surface and wherein the piston (24) comprises a side portion (24B) which faces and/or is in direct contact and/or radially abuts the inner surface, wherein inner surface comprises or forms a sliding/gliding surface for the fluid piston (24).

23. The method according to claim 22, wherein at least one of:
- the fluid piston (24) is provided with at least one circumferential fluid seal (24D) acting between the fluid piston (24) and the container (20),
- the fluid piston (24) is provided with at least one circumferential fluid seal (24D) acting between a side portion (24B) of the fluid piston (24) and the container (20),
- the fluid piston (24) is provided with at least one circumferential fluid seal (24D) acting between the fluid piston (24) and an inner surface of the container (20),
- the side portion (24B) of the fluid piston comprises or forms a fluid seal (24D), and
- the fluid seal (24D) is formed integrally.

24. The method according to claim 1, wherein at least one of:
- the fluid piston (24) comprises a plurality of fluid seals (24D),
- the fluid piston (24) comprises a plurality of two fluid seals (24D), and
- the plurality of fluid seals (24D) are axially spaced apart from one another.

25. The method according to claim 1, wherein an at least essentially pressure-free cartridge (3) is produced.

26. The method according to claim 1, wherein the bottom side (20D) of the container (20) is sealed by means of a base seal (25).

27. The method according to claim 1, wherein at least one of:
- the closure part (23) is secured to the container (20), and
- the closure part (23) is secured to the container (20) by means of a securing element (36) crimped thereto and/or in a form-fitting manner.

28. A method for producing a cartridge (3), comprising the steps of:
- providing a container (20), which includes engaging elements on at least one of a proximal end and a distal end of the container (20) that are adapted for insertion of the cartridge (3) into, and retaining thereof within, a housing of a dispensing device;
- providing a closure part (23) and a fluid piston (24);

arranging the fluid piston (24) in the container (20);
filling a fluid (2) into an opening (20G) of the container (20); and
inserting the closure part (23) into the opening (20G), such that the fluid piston (24) arranged within the container (20) is moved,
wherein at least one of:
an opening (23D) of the closure part (23) is sealed,
the opening (23D) of the closure part (23) is sealed by means of a securing element (36) and/or by attaching a closure seal (23E) to the closure part (23).

29. A method for producing a cartridge (3), comprising the steps of:
providing a container (20), which includes engaging elements on at least one of a proximal end and a distal end of the container (20) that are adapted for insertion of the cartridge (3) into, and retaining thereof within, a housing of a dispensing device;
providing a closure part (23) and a fluid piston (24);
arranging the fluid piston (24) in the container (20);
filling a fluid (2) into an opening (20G) of the container (20); and
inserting the closure part (23) into the opening (20G), such that the fluid piston (24) arranged within the container (20) is moved,
wherein at least one of: (i) the closure part comprises an outer/flange portion (23A) and an end/tapered portion (23C), (ii) the outer portion (23A) and the end portion (23C) each comprises or forms an axial end of the closure part (23), (iii) the outer diameter of the outer portion (23A) is larger than the outer diameter of the end portion (23C), (iv) the outer portion (23A) is arranged on a side facing away from the interior of the container (20), and (v) the end portion (23C) is arranged on a side facing the interior of the container (20); and
wherein at least one of: (vi) the outer portion (23A) is flange-like and/or abuts axially the container (20), forming an axial sealing (S2); and (vii) the outer portion (23A) includes a top portion (20C) and/or top side (20F) forming an axial sealing (S2).

* * * * *